(12) United States Patent
Bechtel et al.

(10) Patent No.: US 11,419,528 B2
(45) Date of Patent: *Aug. 23, 2022

(54) TISSUE OXIMETER WITH STORED SIMULATED REFLECTANCE CURVES

(71) Applicant: ViOptix, Inc., Newark, CA (US)

(72) Inventors: Kate LeeAnn Bechtel, Pleasant Hill, CA (US); H. Keith Nishihara, Los Altos, CA (US)

(73) Assignee: ViOptix, Inc., Newark, CA (US)

( * ) Notice: Subject to any disclaimer, the term of this patent is extended or adjusted under 35 U.S.C. 154(b) by 587 days.

This patent is subject to a terminal disclaimer.

(21) Appl. No.: 16/281,049

(22) Filed: Feb. 20, 2019

(65) Prior Publication Data

US 2019/0175084 A1 Jun. 13, 2019

Related U.S. Application Data

(63) Continuation of application No. 15/163,565, filed on May 24, 2016, now Pat. No. 10,213,142, which is a
(Continued)

(51) Int. Cl.
*A61B 5/1455* (2006.01)
*A61B 90/00* (2016.01)
(Continued)

(52) U.S. Cl.
CPC ........ *A61B 5/14551* (2013.01); *A61B 5/0059* (2013.01); *A61B 5/0075* (2013.01);
(Continued)

(58) Field of Classification Search
None
See application file for complete search history.

(56) References Cited

U.S. PATENT DOCUMENTS 4,223,680 A 9/1980 Jobsis
4,286,599 A 9/1981 Hahn et al.
(Continued)

FOREIGN PATENT DOCUMENTS

JP 05-261088 10/1993
KR 10-2009-0016744 2/2009

OTHER PUBLICATIONS

Alexandrakis, et al., "Accuracy of the Diffusion Approximation in Determining the Optical Properties of a Two-Layer Turbid Medium," Applied Optics, vol. 37, No. 31, Nov. 1, 1998, pp. 7403-7409.
(Continued)

*Primary Examiner* — Marjan Fardanesh
(74) *Attorney, Agent, or Firm* — Aka Chan LLP

(57) ABSTRACT

A method for determining oxygen saturation includes emitting light from sources into tissue; detecting the light by detectors subsequent to reflection; and generating reflectance data based on detecting the light. The method includes determining a first subset of simulated reflectance curves from a set of simulated reflectance curves stored in a tissue oximetry device for a coarse grid; and fitting the reflectance data points to the first subset of simulated reflectance curves to determine a closest fitting one of the simulated reflectance curves. The method includes determining a second subset of simulated reflectance curves for a fine grid based on the closest fitting one of the simulated reflectance curves; determining a peak of absorption and reflection coefficients from the fine grid; and determining an absorption and a reflectance coefficient for the reflectance data points by performing a weighted average of the absorption coefficients and reflection coefficients from the peak.

81 Claims, 8 Drawing Sheets

Related U.S. Application Data continuation of application No. 13/887,220, filed on May 3, 2013, now Pat. No. 9,345,439.

(60) Provisional application No. 61/682,146, filed on Aug. 10, 2012, provisional application No. 61/642,399, filed on May 3, 2012, provisional application No. 61/642,389, filed on May 3, 2012, provisional application No. 61/642,395, filed on May 3, 2012, provisional application No. 61/642,393, filed on May 3, 2012.

(51) Int. Cl.
*A61B 5/00* (2006.01)
*A61B 5/1495* (2006.01)
*A61M 35/00* (2006.01)
*A61B 5/145* (2006.01)
*A61B 90/11* (2016.01)
*A61B 5/1459* (2006.01)
*A61B 90/30* (2016.01)

(52) U.S. Cl.
CPC .......... *A61B 5/1455* (2013.01); *A61B 5/1459* (2013.01); *A61B 5/1495* (2013.01); *A61B 5/14546* (2013.01); *A61B 5/14552* (2013.01); *A61B 5/72* (2013.01); *A61B 5/7246* (2013.01); *A61B 5/7282* (2013.01); *A61B 5/74* (2013.01); *A61B 5/742* (2013.01); *A61B 5/7405* (2013.01); *A61B 5/7475* (2013.01); *A61B 90/11* (2016.02); *A61B 90/39* (2016.02); *A61M 35/003* (2013.01); *A61B 2090/065* (2016.02); *A61B 2090/306* (2016.02); *A61B 2090/395* (2016.02); *A61B 2560/0431* (2013.01); *A61B 2560/0475* (2013.01); *A61B 2562/0271* (2013.01); *A61B 2562/166* (2013.01)

(56) References Cited

U.S. PATENT DOCUMENTS

| | | | |
|---|---|---|---|
| 5,088,493 A | 2/1992 | Giannini et al. |
| 5,218,962 A | 6/1993 | Mannheimer et al. |
| 5,517,301 A | 5/1996 | Dave |
| 5,517,987 A | 5/1996 | Tsuchiya |
| 5,690,113 A | 11/1997 | Sliwa et al. |
| 6,056,692 A | 5/2000 | Schwartz |
| 6,070,093 A | 5/2000 | Oosta et al. |
| 6,078,833 A | 6/2000 | Hueber |
| 6,197,034 B1 | 3/2001 | Gvozdic et al. |
| 6,285,904 B1 | 9/2001 | Weber et al. |
| 6,453,183 B1 | 9/2002 | Walker |
| 6,516,209 B2 | 2/2003 | Cheng et al. |
| 6,549,284 B1 | 4/2003 | Boas et al. |
| 6,587,701 B1 | 7/2003 | Stranc et al. |
| 6,587,703 B2 | 7/2003 | Cheng et al. |
| 6,597,931 B1 | 7/2003 | Cheng et al. |
| 6,708,048 B1 | 3/2004 | Chance |
| 6,766,188 B2 | 7/2004 | Soller |
| 6,839,580 B2 | 1/2005 | Zonios et al. |
| 7,247,142 B1 | 7/2007 | Elmandjra et al. |
| 7,254,427 B2 | 8/2007 | Cho et al. |
| 7,344,587 B2 | 3/2008 | Kahn et al. |
| D567,949 S | 4/2008 | Lash et al. |
| 7,355,688 B2 | 4/2008 | Lash et al. |
| D568,479 S | 5/2008 | Mao et al. |
| 7,657,293 B2 | 2/2010 | Lash et al. |
| 8,798,700 B1 | 8/2014 | Heaton et al. |
| 2002/0019587 A1 | 2/2002 | Cheng et al. |
| 2002/0179094 A1 | 12/2002 | Perlow |
| 2004/0111016 A1 | 6/2004 | Casscells et al. |
| 2004/0260161 A1 | 12/2004 | Melker |
| 2005/0177069 A1 | 8/2005 | Takizawa et al. |
| 2005/0250998 A1 | 11/2005 | Huiku |
| 2005/0277818 A1 | 12/2005 | Myers |
| 2006/0129037 A1 | 6/2006 | Kaufman et al. |
| 2007/0149886 A1 | 6/2007 | Kohls |
| 2008/0015422 A1 | 1/2008 | Wessel |
| 2008/0015424 A1 | 1/2008 | Bernreuter |
| 2008/0139908 A1 | 6/2008 | Kurth |
| 2008/0181715 A1 | 7/2008 | Cohen |
| 2005/0319290 | 12/2008 | Mao et al. |
| 2008/0319290 A1 | 12/2008 | Mao et al. |
| 2009/0234209 A1 | 9/2009 | Lash et al. |
| 2009/0275805 A1 | 11/2009 | Lane et al. |
| 2010/0010486 A1 | 1/2010 | Mehta et al. |
| 2011/0028814 A1 | 2/2011 | Petersen et al. |
| 2011/0046458 A1 | 2/2011 | Pinedo et al. |

OTHER PUBLICATIONS

Cen, et al., "Optimization of Inverse Algorithm for Estimating the Optical Properties of Biological Materials Using Spatially-Resolved Diffuse Reflectance," Inverse Problems in Science and Engineering, vol. 18, No. 6, Sep. 2010, pp. 853-872.

Dam, et al., "Determination of Tissue Optical Properties from Diffuse Reflectance Profiles by Multivariate Calibration," Applied Optics, vol. 37, No. 4, Feb. 1, 1998, pp. 772-778.

Farrell, et al., "Influence of Layered Tissue Architecture on Estimates of Tissue Optical Properties Obtained from Spatially Resolved Diffuse Reflectometry," Applied Optics, vol. 37, No. 10, Apr. 1, 1998, pp. 1958-1972.

Fawzi, et al., "Determination of the Optical Properties of a Two-Layer Tissue Model by Detecting Photons Migrating at Progressively Increasing Depths," Applied Optics, vol. 42, No. 31, Nov. 1, 2003, pp. 6398-6411.

Kienle, et al., "Spatially Resolved Absolute Diffuse Reflectance Measurements for Noninvasive Determination of the Optical Scattering and Absorption Coefficients of Biological Tissue," Applied Optics, vol. 35, No. 13, May 1, 1996, pp. 2304-2314.

Nichols, et al., "Design and Testing of a White-Light, Steady-State Diffuse Reflectance Spectrometer for Determination of Optical Properties of Highly Scattering Systems," Applied Optics, vol. 36, No. 1, Jan. 1, 1997, pp. 93-104.

Seo, et al., "Perturbation and Differential Monte Carlo Methods for Measurement of Optical Properties in a Layered Epithelial Tissue Model," Journal of Biomedical Optics, vol. 12(1), 014030, Jan./Feb. 2007, pp. 1-15.

Tseng, et al., "In Vivo Determination of Skin Near-Infrared Optical Properties Using Diffuse Optical Spectroscopy," Journal of Biomedical Optics, vol. 13(1), 014016, Jan./Feb. 2008, pp. 1-7.

Tseng, et al., "Analysis of a Diffusion-Model-Based Approach for Efficient Quantification of Superficial Tissue Properties," Optics Letters, vol. 35, No. 22, Nov. 15, 2010, pp. 3739-3741.

TISSUE OXIMETER WITH STORED SIMULATED REFLECTANCE CURVES

CROSS-REFERENCE TO RELATED APPLICATIONS

This patent application is a continuation of U.S. patent application Ser. No. 15/163,565, filed May 24, 2016, issued as U.S. Pat. No. 10,213,142 on Feb. 26, 2019, which is a continuation of U.S. patent application Ser. No. 13/887,220, filed May 3, 2013, issued as U.S. Pat. No. 9,345,439 on May 24, 2016, which claims the benefit of U.S. patent applications 61/642,389, 61/642,393, 61/642,395, and 61/642,399, filed May 3, 2012, and 61/682,146, filed Aug. 10, 2012. These applications are incorporated by reference along with all other references cited in this application.

BACKGROUND OF THE INVENTION

The present invention relates generally to optical systems that monitor oxygen levels in tissue. More specifically, the present invention relates to optical probes, such as oximeters, that include sources and detectors on sensor heads of the optical probes and that use locally stored simulated reflectance curves for determining oxygen saturation of tissue.

Oximeters are medical devices used to measure oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or person training for a marathon); and veterinary purposes (e.g., animal monitoring).

Pulse oximeters and tissue oximeters are two types of oximeters that operate on different principles. A pulse oximeter requires a pulse in order to function. A pulse oximeter typically measures the absorbance of light due to the pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated and deoxygenated hemoglobins, melanin, water, lipid, and cytochrome. Oxygenated and deoxygenated hemoglobins are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving measurement accuracy; reducing measurement time; lowering cost; reducing size, weight, or form factor; reducing power consumption; and for other reasons, and any combination of these.

In particular, assessing a patient's oxygenation state, at both the regional and local level, is important as it is an indicator of the state of the patient's health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of non-ideal conditions. While existing oximeters have been sufficient for post-operative tissue monitoring where absolute accuracy is not critical and trending data alone is sufficient, accuracy is, however, required during surgery in which spot-checking can be used to determine whether tissue might remain viable or needs to be removed.

Therefore, there is a need for an improved tissue oximetry probes and methods of making measurements using these probes.

BRIEF SUMMARY OF THE INVENTION

A tissue oximetry device utilizes a relatively large number of simulated reflectance curves to quickly determine the optical properties of tissue under investigation. The optical properties of the tissue allow for the further determination of the oxygenated hemoglobin and deoxygenated hemoglobin concentrations of the tissue as well as the oxygen saturation of the tissue.

According to a specific embodiment, a method for determining oxygen saturation of tissue via a tissue oximetry device includes emitting light from a set of light sources into tissue; detecting the light by a plurality of detectors subsequent to reflection of the light from the tissue; and generating reflectance data points for the tissue based on detecting the light by the plurality of detectors. The method further includes determining a first subset of simulated reflectance curves from a set of simulated reflectance curves stored in the tissue oximetry device for a coarse grid; and fitting the reflectance data points to the first subset of simulated reflectance curves included in the coarse grid to determine a closest fitting one of the simulated reflectance curves included in the coarse grid. The method further includes determining a second subset of simulated reflectance curves from the set of simulated reflectance curves stored in the tissue oximetry device for a fine grid based on the closest fitting one of the simulated reflectance curves included in the coarse grid. The method further includes determining a peak surface array of absorption coefficients and reflection coefficients from the fine grid; and determining an absorption coefficient and a reflectance coefficient for the reflectance data points by performing a weighted average of the absorption coefficients and reflection coefficients from the peak surface array. The weighted average may be a centroid calculation.

According to a specific implementation of the method, fitting the reflectance data points to a subset of simulated reflectance curves included in the coarse grid includes calculating a sum of squares error between the reflectance data points and each of the simulated reflectance curves of the coarse grid. According to another specific embodiment of the method, fitting the reflectance data points to a subset of simulated reflectance curves included in the fine grid includes calculating a sum of squares error between the reflectance data points and each of the simulated reflectance curves of the fine grid.

According to a specific implementation, the method further includes determining an oxygen saturation value for the tissue based on the scattering coefficient and the absorption coefficients for the tissue. Determining the oxygen saturation includes generating a look-up table of oxygen saturation values for finding a best fit of absorption coefficients based on a range of probable total hemoglobin, melanin, and oxygen saturation values. Determining the oxygen saturation may further include converting the absorption coefficients to a unit vector; dividing the unit vector by a norm of the unit vector to reduce systematic error; and comparing the unit vector to the look-up table to find a best fit of the unit vector to the oxygen saturations of the look-up table.

According to another embodiment, a tissue oximetry device includes a processor; a memory storing a plurality of simulated reflectance curves; a light source configured to be controlled by the processor; and a plurality of detectors configured to be controlled by the processor; wherein the processor is configured to: control the light source to emit light into tissue; control the detectors to detect the light subsequent to reflection of the light from the tissue; control the detectors to generate reflectance data based on detecting the light; determine a first subset of simulated reflectance curves from a set of simulated reflectance curves stored in the tissue oximetry device for a coarse grid; fit the reflectance data points to the first subset of simulated reflectance curves included in the coarse grid to determine a closest fitting one of the simulated reflectance curves included in the coarse grid; determine a second subset of simulated reflectance curves from the set of simulated reflectance curves stored in the tissue oximetry device for a fine grid based on the closest fitting one of the simulated reflectance curves included in the coarse grid; and fit the reflectance data points to the second subset of simulated reflectance curves included in the fine grid to determine a closest fitting one of the simulated reflectance curves included in the fine grid, wherein one of the simulated reflectance curve from the fine grid that closest fits the reflectance data points represents a scattering coefficient and an absorption coefficient for the tissue.

In one implementation, the tissue oximetry device can measure oxygen saturation without requiring a pulse or heart beat. A tissue oximetry device of the invention is applicable to many areas of medicine and surgery including plastic surgery. The tissue oximetry device can make oxygen saturation measurements of tissue where there is no pulse. Such tissue may have been separated from the body (e.g., a flap) and will be transplanted to another place in the body. Aspects of the invention may also be applicable to a pulse oximeter. In contrast to a tissue oximetry device, a pulse oximeter requires a pulse in order to function. A pulse oximeter typically measures the absorbance of light due to the pulsing arterial blood.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
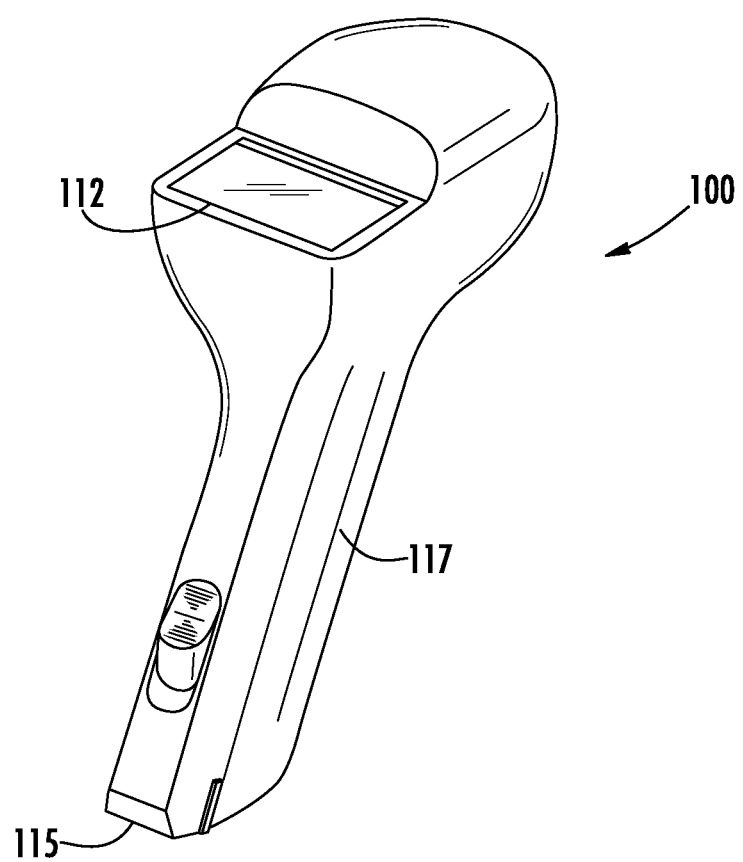
FIG. 1 is a simplified image of a tissue oximetry device according to one embodiment.

FIG. 1 is a simplified image of a tissue oximetry device 100 according to one embodiment. Tissue oximetry device 100 is configured to make tissue oximetry measurements, such as intraoperatively and postoperatively. Tissue oximetry device 100 may be a handheld device that includes a tissue oximetry probe 115 (also referred to as a sensor head), which may be positioned at an end of a sensing arm 117. Tissue oximetry device 100 is configured to measure the oxygen saturation of tissue by emitting light, such as near-infrared light, from tissue oximetry probe 115 into tissue, and collecting light reflected from the tissue at the tissue oximetry probe.

Tissue oximetry device 100 may include a display 112 or other notification device that notifies a user of oxygen saturation measurements made by the tissue oximetry device. While tissue oximetry probe 115 is described as being configured for use with tissue oximetry device 100, which is a handheld device, tissue oximetry probe 115 may be used with other tissue oximetry devices, such as a modular tissue oximetry device where the tissue oximetry probe is at the end of a cable device that couples to a base unit. The cable device might be a disposable device that is configured for use with one patient and the base unit might be a device that is configured for repeated use. Such modular tissue oximetry devices are well understood by those of skill in the art and are not described further.

Figure 2A:
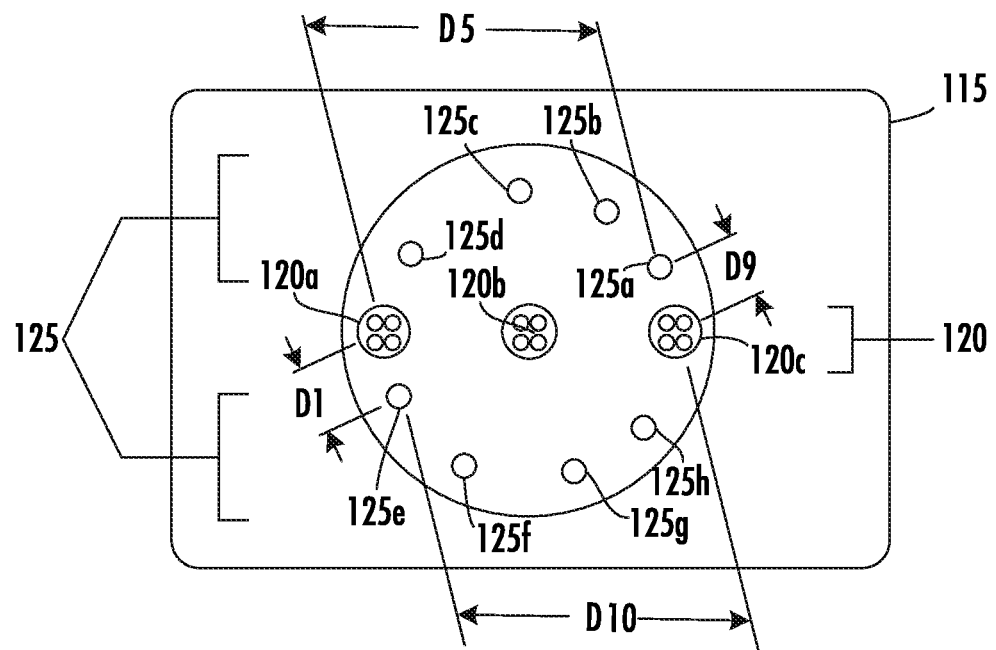
FIGS. 2A and 2B are simplified end views of a tissue oximetry probe of the tissue oximetry device according to a pair of alternative embodiments.
Figure 2B:
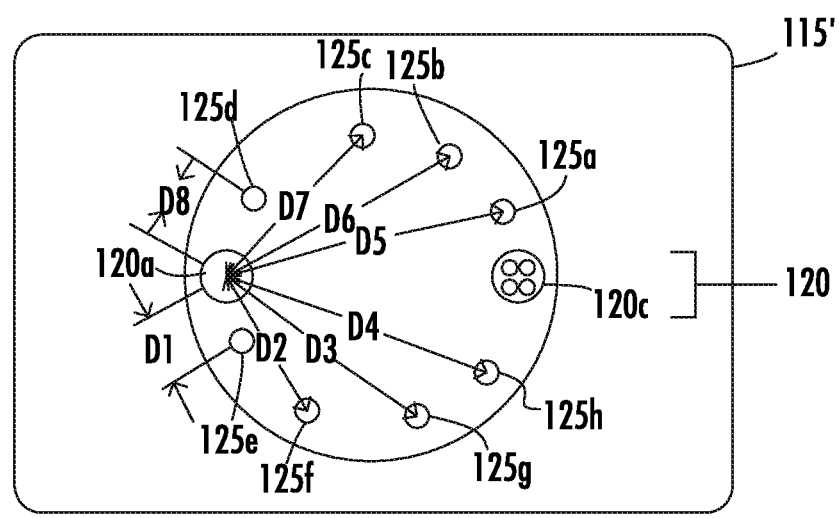

FIG. 2A is a simplified end view of tissue oximetry probe 115 according to one embodiment. Tissue oximetry probe 115 is configured to contact tissue (e.g., a patient's skin) for which a tissue oximetry measurement is to be made. Tissue oximetry probe 115 includes a set of light sources 120 (generally light sources 120) and includes a set of detectors 125 (generally detectors 125). The set of light sources 120 may include two or more light sources. According to the embodiment shown in FIG. 2A, tissue oximetry probe 115 includes three light sources 120a, 120b, and 120c, but may alternatively include two light sources, such as light sources 120a and 120c where light source 120b is omitted. Additional light sources (not shown) can be added. FIG. 2B is a simplified end view of a tissue oximetry probe 115' according to an embodiment where the tissue oximetry probe includes the two light sources 120a and 120c, but does not include light source 120b. Aside from the different number of light sources, tissue oximetry probes 115 and 115' are substantially similar.

The set of detectors 125 may include eight detectors 125a, 125b, 125c, 125d, 125e, 125f, 125g, and 125h as shown, but may include more or fewer detectors. Detectors 125 are positioned with respect to outer light sources 120a and 120c such that eight or more (e.g., fourteen) unique source-to-detector distances are created. The shortest source-to-detector distances may be the same. For example, the shortest source-to-detector distance D1 between light source 120a and detector 125e, and the shortest source-to-detector distance D9 between light source 120c and detector 125a may be the same. It follows that the source-to-detector distance D5 between light source 120a and detector 125a, and the source-to-detector distance D10 between light source 120c and detector 125e may also be the same. The source-to-detector distances D5 and D10 are the longest source-to-detector distance for light sources 120a and 120c.

With the exception of the shortest source-to-detector distance and the longest source-to-detector distance for light sources 120a and 120c, the source-to-detector distances for light sources 120a and 120c may be unique. As described above, tissue oximetry probe 115 may have fourteen unique source-to-detector distances that allow for fourteen reflectance data points to be collected by detectors 125 from light emitted from light sources 120a and 120c.

Furthermore, the source-to-detector distances for light sources 120a and 120c may also be selected such that the increases in the distances are substantially uniform. Thereby, a plot of source-to-detector distance verses reflectance detected by detectors 125 can provide a reflectance curve where the data points are well spaced along the x-axis. These spacings of the distances between light sources 120a and 120c, and detectors 125 reduces data redundancy and can lead to the generation of relatively accurate reflectance curves (further described below).

While the tissue oximetry probes 115 and 115' described above have circularly arranged detectors, the detectors may be positioned in other arrangements, such as randomly, triangular, rectangular, square, ovoid, or the like. In some embodiments, the light sources may also be alternatively arranged, such as randomly, in triangular, rectangular, ovoid, or other shapes.

Figure 3:
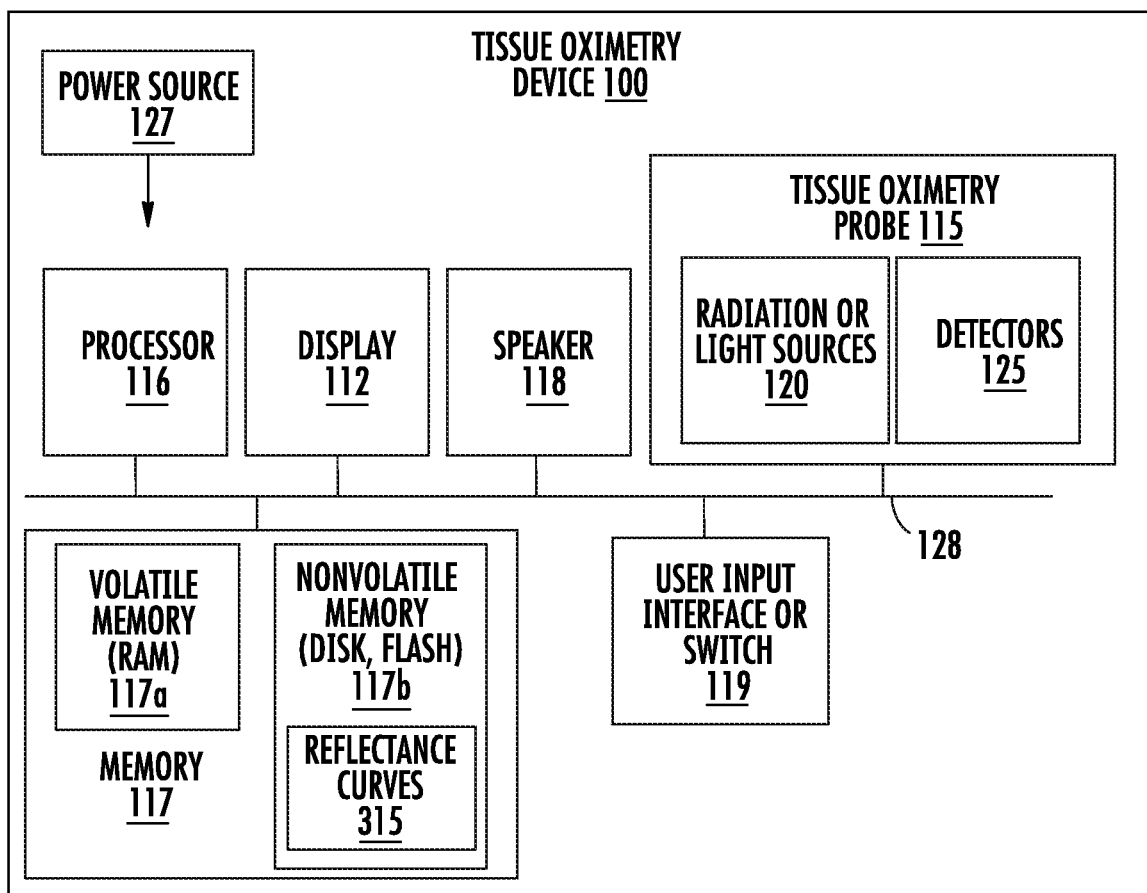
FIG. 3 is a block diagram of the tissue oximetry device according to one embodiment.

FIG. 3 is a block diagram of tissue oximetry device 100 according to one embodiment. Tissue oximetry device 100 includes display 112, a processor 116, a memory 117, a speaker 118, one or more user-selection devices 119 (e.g., one or more switches), a set of light sources 120, a set of detectors 125, and a power source (e.g., a battery) 127. The foregoing listed components may be linked together via a bus 128, which may be the system bus architecture of tissue oximetry device 100. Although this figure shows one bus that connects to each component, the busing is illustrative of any interconnection scheme serving to link these components or other components included in tissue oximetry device 100 subsystems. For example, speaker 118 could be connected to a subsystem through a port or have an internal direct connection to processor 116. Further, the components described are housed in a mobile housing (see FIG. 1) of tissue oximetry device 100 according to at least one embodiment.

Processor 116 may include a microprocessor, a microcontroller, control logic, a multi-core processor, or the like. Memory 117 may include a variety of memories, such as a volatile memory 117a (e.g., a RAM), a nonvolatile memory 117b (e.g., a disk, FLASH, or the like). Different implementations of tissue oximetry device 100 may include any number of the listed components, in any combination or configuration, and may also include other components not shown.

Power source 127 can be a battery, such as a disposable battery. Disposable batteries are discarded after their stored charge is expended. Some disposable battery chemistry technologies include alkaline, zinc carbon, or silver oxide. The battery has sufficient stored charged to allow use of the handheld device for several hours. After use, the handheld unit is discarded.

In other implementations, the battery can also be rechargeable where the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with cord that connects to the handheld unit. The circuitry in the handheld unit can include a recharger circuit (not shown). Batteries with rechargeable battery chemistry may be sometimes used as disposable batteries, where the batteries are not recharged but disposed of after use.

Stored Simulated Reflectance Curves

According to a specific embodiment, memory 117 stores a number of Monte Carlo-simulated reflectance curves 315 ("simulated reflectance curves"), which may be generated by a computer for subsequent storage in the memory. Each of the simulated reflectance curves 315 represents a simulation of light (e.g., near infrared light) emitted from one or more simulated light sources into simulated tissue and reflected from the simulated tissue into one or more simulated detectors. Simulated reflectance curves 315 are for a specific configuration of simulated light sources and simulated detectors, such as the configuration of light sources 120 and detectors 125 in tissue oximetry probes 115, 115', or the like. Therefore, simulated reflectance curves 315 model light emitted from, and collected by, tissue oximetry device 100. Further, each of the simulated reflectance curves 315 represents a unique real tissue condition, such as specific tissue absorption and tissue scattering values that relate to particular concentrations of tissue chromophores and densities of tissue scatterers. The number of simulated reflectance curves stored in memory 117 may be relatively large and can represent nearly all, if not all, practical combinations of optical properties and tissue properties that may be present in real tissue that is analyzed for viability by tissue oximetry device 100. While memory 117 is described herein as storing Monte Carlo-simulated reflectance curves, memory 117 may store simulated reflectance curves generated by methods other than Monte Carlo methods, such as using the diffusion approximation.

Figure 4:
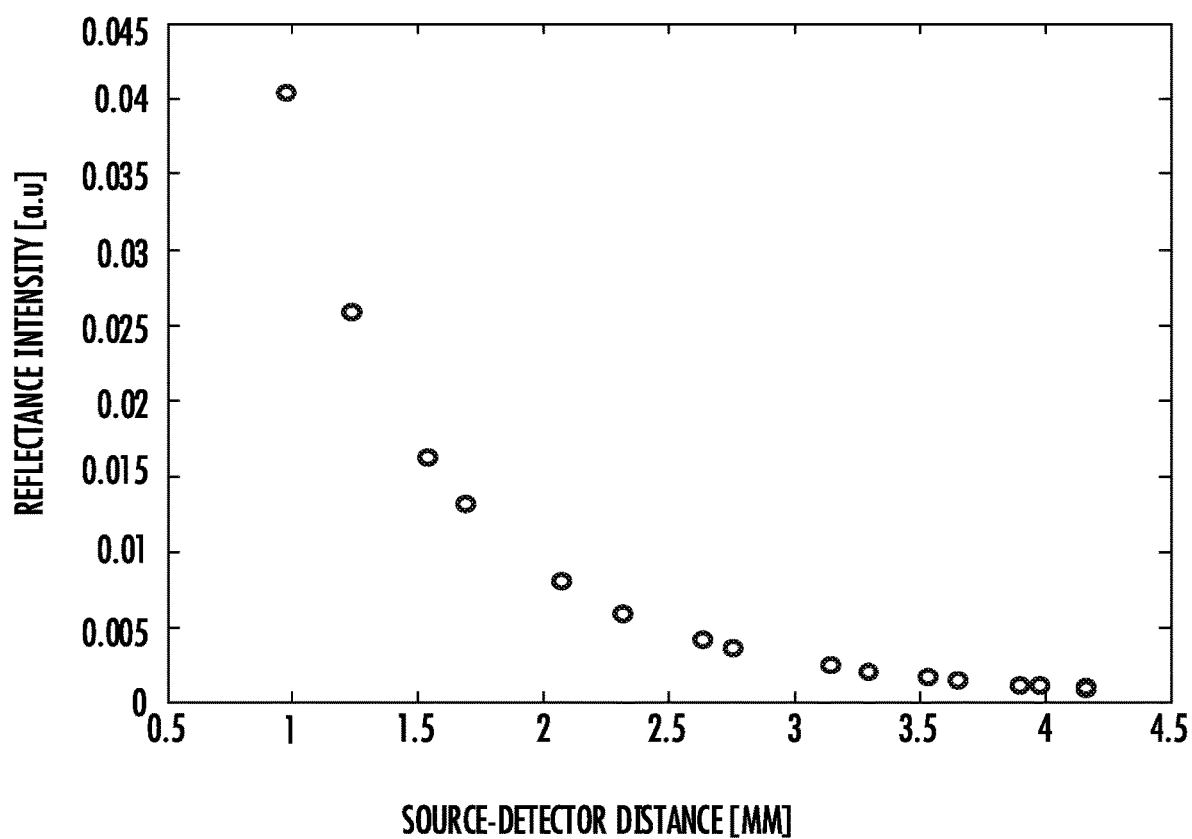
FIG. 4 is an example graph of a number of Monte Carlo-simulated reflectance curves.

FIG. 4 is an example graph of a reflectance curve, which may be for a specific configuration of light sources 120 and detectors 125, such as one of the configurations light sources and detectors of tissue oximetry probes 115, 115', or the like. The horizontal axis of the graph represents the distances between light sources 120 and detectors 125 (i.e., source-detector distances). If the distances between light sources 120 and detectors 125 are appropriately chosen, and the simulated reflectance curve is a simulations for light sources 120 and detectors 125, then the lateral spacings between the data points in the simulated reflectance curve will be relatively uniform. Such relatively uniform spacings can be seen in the simulated reflectance curve in FIG. 4. The vertical axis of the graph represents the simulated reflectance of light that reflects from tissue and is detected by detectors 125. As shown by the simulated reflectance curve, the reflectance that reaches detectors 125 varies with the distance between light sources 120 and detectors 125.

According to one implementation, memory 117 stores a select number of points for each of the simulated reflectance curves 315 and might not store the entirety of the simulated reflectance curves. The number of points stored for each of simulated reflectance curves 315 may match the number of source-detector pairs. For example, if tissue oximetry probe 115 includes two light sources 120a and 120c and includes eight detectors 125a-125h, then tissue oximetry probe 100 includes sixteen source-detector pairs, and memory 117 may thus store sixteen select data points for each of the simulated reflectance curves, where stored data points are for the specific source-detectors distances (i.e., distances between the light sources and the detectors).

Thus, the simulated reflectance curve database stored in memory 117 might be sized 16×3×5850 where sixteen points are stored per curve for three different wavelengths that may be generated and emitted by each light source 210 and wherein there are a total of 5850 curves spanning the optical property ranges. Alternatively, the simulated reflectance curve database stored in memory 117 might be sized 16×4×5850 wherein sixteen points are stored per curve for four different wavelengths that may be generated and emitted by each light source and wherein there are a total of 5850 curves spanning the optical property ranges. The 5850 curves originate, for example, from a matrix of 39 absorption coefficients $\mu_s'$ values and 150 absorption coefficient $\mu_a$ values. The $\mu_s'$ values might range from 5:5:24 centimeter$^{-1}$ ($\mu_s'$ depends on the value for g). The $\mu_a$ values might range from 0.01:0.01:1.5. It will be understood the foregoing described ranges are example ranges and the number source-detectors pairs, the number of wavelengths generated by each light source, and the number of simulated reflectance curves may be smaller or larger.

Tissue Analysis

Figure 5A:
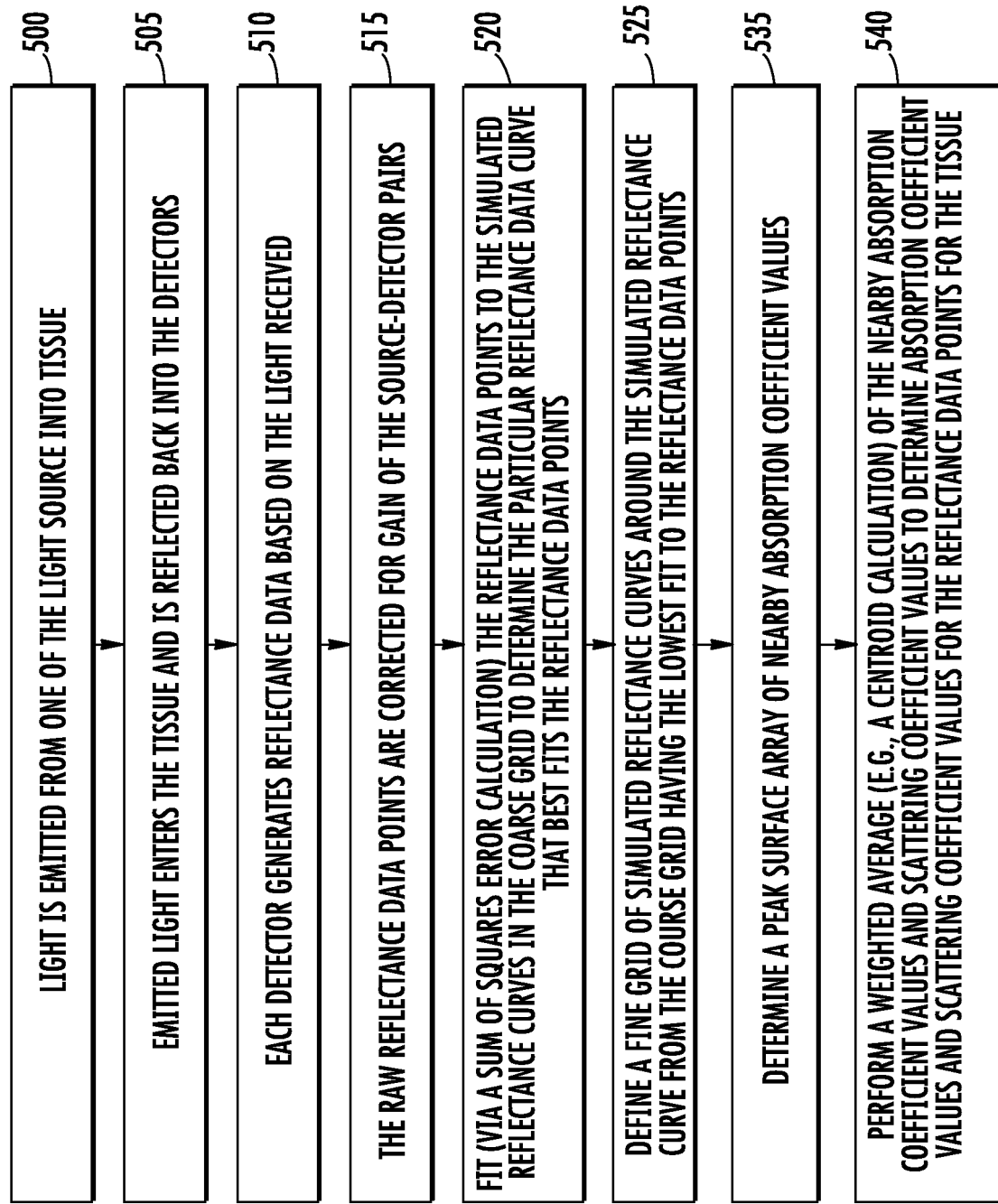
FIG. 5A is a high-level flow diagram of a method for determining the optical properties of tissue (e.g., real tissue) by tissue oximetry device where the tissue oximetry device uses reflectance data and simulated reflectance curves to determine the optical properties.

FIG. 5A is a high-level flow diagram of a method for determining the optical properties of tissue (e.g., real tissue) by tissue oximetry device 100 where the tissue oximetry device uses reflectance data and simulated reflectance curves 315 to determine the optical properties. The optical properties may include the absorption coefficient $\mu_a$ and the scattering coefficients $\mu_s$ of the tissue. A further method for conversion of the absorption coefficient $\mu_a$ and the scattering coefficients of the tissue $\mu_s$ to oxygen saturation values for tissue is described in further detail below. The high-level flow diagram represents one example embodiment. Steps may be added to, removed from, or combined in the high-level flow diagram without deviating from the scope of the embodiment.

At 500, tissue oximetry device 100 emits light (e.g., near infrared light) from one of the light sources 120, such as light source 120a into tissue. The tissue oximetry device is generally in contact with the tissue when the light is emitted from the light source. After the emitted light reflects from the tissue, detectors 125 detect a portion this light, step 505, and generate reflectance data points for the tissue, step 510. Steps 500, 505, and 510 may be repeated for multiple wavelengths of light (e.g., red, near infrared light, or both) and for one or more other light sources, such as light source 120c. The reflectance data points for a single wavelength might include sixteen reflectance data points if, for example, tissue oximetry probe 115 has sixteen source-detectors distances. The reflectance data points are sometimes referred to as an N-vector of the reflectance data points.

At 515, the reflectance data points (e.g., raw reflectance data points) are corrected for gain of the source-detector pairs. During calibration of the source-detector pairs, gain corrections are generated for the source-detector pairs and are stored in memory 117. Generation of the gain corrections are described in further detail below.

At 520, processor 116 fits (e.g., via a sum of squares error calculation) the reflectance data points to the simulated reflectance curves 315 to determine the particular reflectance data curve that best fits (i.e., has the lowest fit error) the reflectance data points. According to one specific implementation, a relatively small set of simulated reflectance curves that are a "coarse" grid of the database of the simulated reflectance curves is selected and utilized for fitting step 520. For example, given 39 scattering coefficient $\mu_s'$ values and 150 absorption coefficient $\mu_a$ values, a coarse grid of simulated reflectance curves might be determined by processor 116 by taking every 5th scattering coefficient $\mu_s'$ value and every 8th absorption coefficients $\mu_a$ for a total of 40 simulated reflectance curves in the coarse grid. It will be understood that the foregoing specific values are for an example embodiment and that coarse grids of other sizes might be utilized by processor 116. The result of fitting the reflectance data points to the coarse grid is a coordinate in the coarse grid $(\mu_a, \mu_s')_{coarse}$ of the best fitting simulated reflectance curve.

At 525, the particular simulated reflectance curve from the coarse grid having the lowest fit error is utilized by processor 116 to define a "fine" grid of simulated reflectance curves where the simulated reflectance curves in the fine grid are around the simulated reflectance curve from the coarse grid having the lowest fit error.

That is, the fine grid is a defined size, with the lowest error simulated reflectance curve from the coarse grid defining the center of the fine grid. The fine grid may have the same number of simulated reflectance curves as the coarse grid or it may have more or fewer simulated reflectance curves. The fine grid is substantially fine so as to provide a sufficient number of points to determine a peak surface array of nearby absorption coefficient $\mu_a$ values and scattering coefficient $\mu_s'$ values, step 530, in the fine grid. Specifically, a threshold may be set by processor 116 utilizing the lowest error value from the coarse grid plus a specified offset. The positions of the scattering coefficient $\mu_s'$ and the absorption coefficient $\mu_a$ on the fine grid that have errors below the threshold may all be identified for use in determining the peak surface array for further determining the scattering coefficient $\mu_s'$ and the absorption coefficient $\mu_a$ for the reflectance data. Specifically, an error fit is made for the peak to determine the absorption coefficient $\mu_a$ and the scattering coefficient $\mu_s'$ values at the peak. A weighted average (e.g., a centroid calculation) of the absorption coefficient $\mu_a$ and the scattering coefficient $\mu_s'$ values at the peak may be utilized by the tissue oximetry device for the determination of the absorption coefficient $\mu_a$ and the scattering coefficient $\mu_s'$ values for the reflectance data points for the tissue, step 540.

Weights for the absorption coefficient $\mu_a$ and the scattering coefficient $\mu_s'$ values for the weighted average may be determined by processor 116 as the threshold minus the fine grid error. Because points on the fine grid are selected with errors below the threshold, this gives positive weights. The weighted calculation of the weighted average (e.g., centroid calculation) renders the predicted scattering coefficient $\mu_s'$ and absorption coefficient $\mu_a$ (i.e., $(\mu_a, \mu_s')_{fine}$) for the reflectance data points for the tissue. Other methods may be utilized by the tissue oximetry device, such as fitting with one or more of a variety of non-linear least squares to determine the true minimum error peak for the scattering coefficient us.

According to one implementation, processor 116 calculates the log of the reflectance data points and the simulated reflectance curves, and divides each log by the square root of the source-detector distances (e.g., in centimeters). These log values divided by the square root of the of the source-detector distances may be utilized by processor 116 for the reflectance data points and the simulated reflectance curves in the foregoing described steps (e.g., steps 515, 520, 525, and 530) to improve the fit of the reflectance data points to the simulated reflectance curves.

According to another implementation, the offset is set essentially to zero, which effectively gives an offset of the difference between the coarse grid minimum and the fine grid minimum. The method described above with respect to FIG. 5A relies on minimum fit error from the coarse grid, so the true minimum error on the fine grid is typically lower. Ideally, the threshold is determined from the lowest error on the fine grid, which would typically require additional computation by the processor.

Figure 5B:
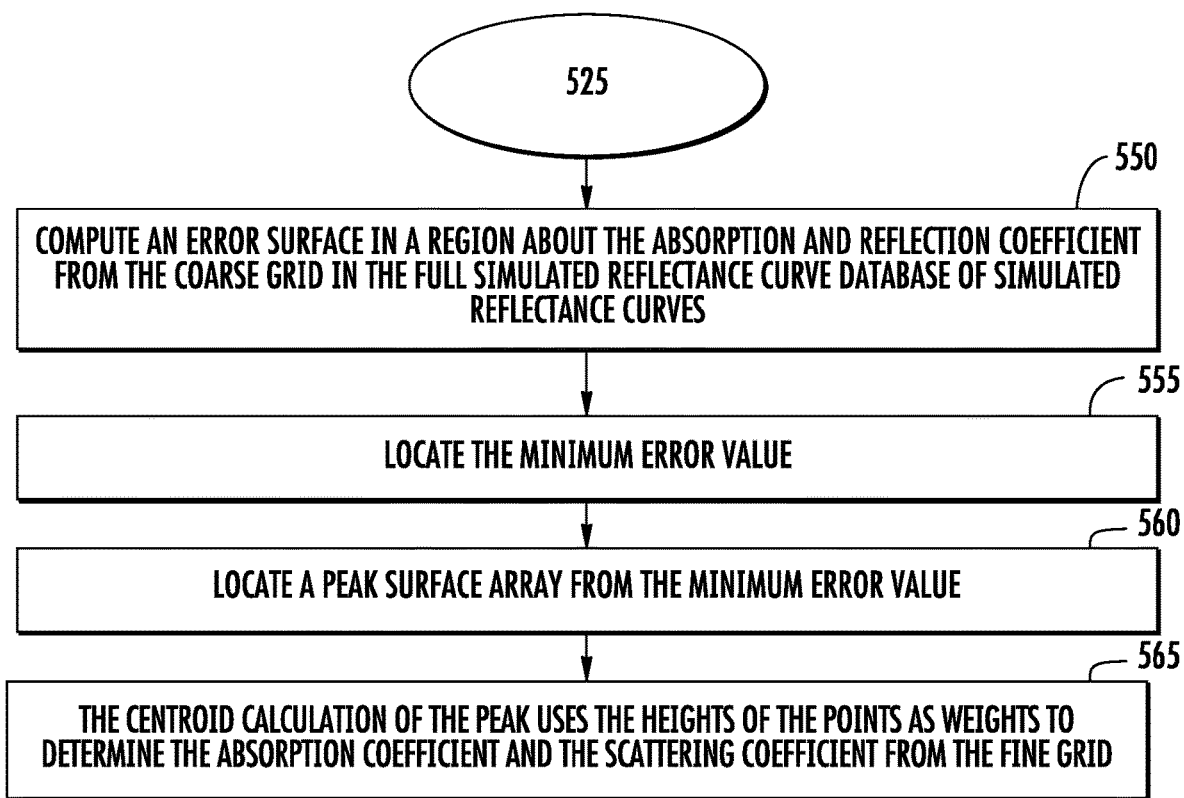
FIG. 5B is a high-level flow diagram of a method for finding the particular simulated reflectance curve that best bits the reflectance data points in the fine grid according to one implementation.

The following is a further detailed description for finding the particular simulated reflectance curve that best fits the reflectance data points in the fine grid according to one implementation. FIG. 5B is a high-level flow diagram of a method for finding the particular simulated reflectance curve that best fits the reflectance data points in the fine grid according to one implementation. The high-level flow diagram represents one example embodiment. Steps may be added to, removed from, or combined in the high-level flow diagram without deviating from the scope of the embodiment.

Subsequent to determining the particular simulated reflectance curve $(\mu_a, \mu_s')_{coarse}$ from the coarse grid that best fits the reflectance data points at step 525, processor 116 computes an error surface in a region about $(\mu_a, \mu_s')_{coarse}$ in the full simulated reflectance curve database (i.e., 16×3×5850 $(\mu_a, \mu_s')$ database) of simulated reflectance curves, step 550. The error surface is denoted as: $err(\mu_a, \mu_s')$. Thereafter, processor 116 locates the minimum error value in $err(\mu_a, \mu_s')$, which is referred to as $err_{min}$, step 555. Processor 116 then generates a peak surface array from $err(\mu_a, \mu_s')$ that is denoted by $pksurf(\mu_a,\mu_s')=k+err_{min}-err(\mu_a, \mu_s')$ if the peak surface is greater than zero, or $pksurf(\mu_a, \mu_s')=k+err_{min}-err(\mu_a, \mu_s')=0$ if the peak surface is less than or equal to zero, step 560. In the expression k is chosen from a peak at the minimum point of $err(\mu_a, \mu_s')$ with a width above zero of approximately ten elements. The center-of-mass (i.e., the centroid calculation) of the peak in $pksurf(\mu_a, \mu_s')$ uses the heights of the points as weights, step 565. The position of the center-of-mass is the interpolated result for the absorption coefficient $\mu_a$ and the scattering coefficient $\mu_s'$ for the reflectance data points for the tissue The method described above with respect to FIGS. 5A and 5B for determining the absorption coefficient $\mu_a$ and the scattering coefficient $\mu_s'$ for reflectance data points for tissue may be repeated for each of the wavelengths (e.g., 3 or 4 wavelengths) generated by each of light sources 120.

Oxygen Saturation Determination

According to a first implementation, processor 116 determines the oxygen saturation for tissue that is probed by tissue oximetry device 100 by utilizing the absorption coefficients $\mu_a$ (e.g., 3 or 4 absorption coefficients $\mu_a$) that are determined (as described above) for the 3 or 4 wavelengths of light that are generated by each light source 120. According to a first implementation, a look-up table of oxygen saturation values is generated for finding the best fit of the absorption coefficients $\mu_a$ to the oxygen saturation. The look-up table may be generated by assuming a range of likely total hemoglobin, melanin, and oxygen saturation values and calculating $\mu_a$ for each of these scenarios. Then, the absorption coefficient $\mu_a$ points are converted to a unit vector by dividing by a norm of the unit vector to reduce systematic error and only depend on relative shape of curve. Then the unit vector is compared to the look-up table to find the best fit, which gives the oxygen saturation.

According to a second implementation, processor 116 determines the oxygen saturation for the tissue by calculating the net analyte signal (NAS) of deoxygenated hemoglobin and oxygenated hemoglobin. The NAS is defined as the portion of the spectrum that is orthogonal to the other spectral components in the system. For example, the NAS of deoxygenated hemoglobin is the portion of the spectrum that is orthogonal to oxygenated hemoglobin spectrum and melanin spectrum. The concentrations of deoxygenated and oxygenated hemoglobin can then be calculated by vector multiplying the respective NAS and dividing by a norm of the NAS squared. Oxygen saturation is then readily calculated as the concentration of oxygenated hemoglobin divided by the sum of oxygenated hemoglobin and deoxygenated hemoglobin. Anal. Chem. 58:1167-1172 (1986) by Lorber is incorporated by reference herein and provides a framework for a further detailed understanding of the second implementation for determining the oxygen saturation for the tissue.

According to one embodiment of tissue oximetry device 100, the reflectance data is generated by detectors 125 at 30 Hertz, and oxygen saturation values are calculated at approximately 3 Hertz. A running average of determined oxygen saturation values (e.g., at least three oxygen saturation values) may be displayed on display 112, which might have an update rate of 1 Hertz.

Optical Properties

As described briefly above, each simulated reflectance curve 315 that is stored in memory 117 represents unique optical properties of tissue. More specifically, the unique shapes of the simulated reflectance curves, for a given wavelength, represent unique values of the optical properties of tissue, namely the scattering coefficient ($\mu_s$), the absorption coefficient ($\mu_a$), the anisotropy of the tissue (g), and index of refraction of the tissue from which the tissue properties may be determined.

The reflectance detected by detectors 125 for relatively small source-to-detector distances is primarily dependent on the reduced scattering coefficient, $\mu_s'$. The reduced scattering coefficient is a "lumped" property that incorporates the scattering coefficient $\mu_s$ and the anisotropy g of the tissue where $\mu_s'=\mu_s(1-g)$, and is used to describe the diffusion of photons in a random walk of many steps of size of $1/\mu_s'$ where each step involves isotropic scattering. Such a description is equivalent to a description of photon movement using many small steps $1/\mu_s$ which each involve only a partial deflection angle if there are many scattering events before an absorption event, i.e., $\mu_a \ll \mu_s'$.

In contrast, the reflectance that is detected by detectors 125 for relatively large source-detector distances is primarily dependent on the effective absorption coefficient $\mu_{eff}$, which is defined as $\sqrt{3\mu_a(\mu_a+\mu_s')}$, which is a function of both $\mu_a$ and $\mu_s'$.

Thus, by measuring reflectance at relatively small source-detector distances (e.g., D1 between light source 120a and detector 125e and D9 between light source 120c and detector 125a) and relatively large source-detector distances (e.g., D5 between light source 120a and detector 125a and D10 between light source 120c and detector 125e), both $\mu_a$ and $\mu_s'$ can be independently determined from one another. The optical properties of the tissue can in turn provide sufficient information for the calculation of oxygenated hemoglobin and deoxygenated hemoglobin concentrations and hence the oxygen saturation of the tissue.

Iterative Fit for Data Collection Optimization.

Figure 6:
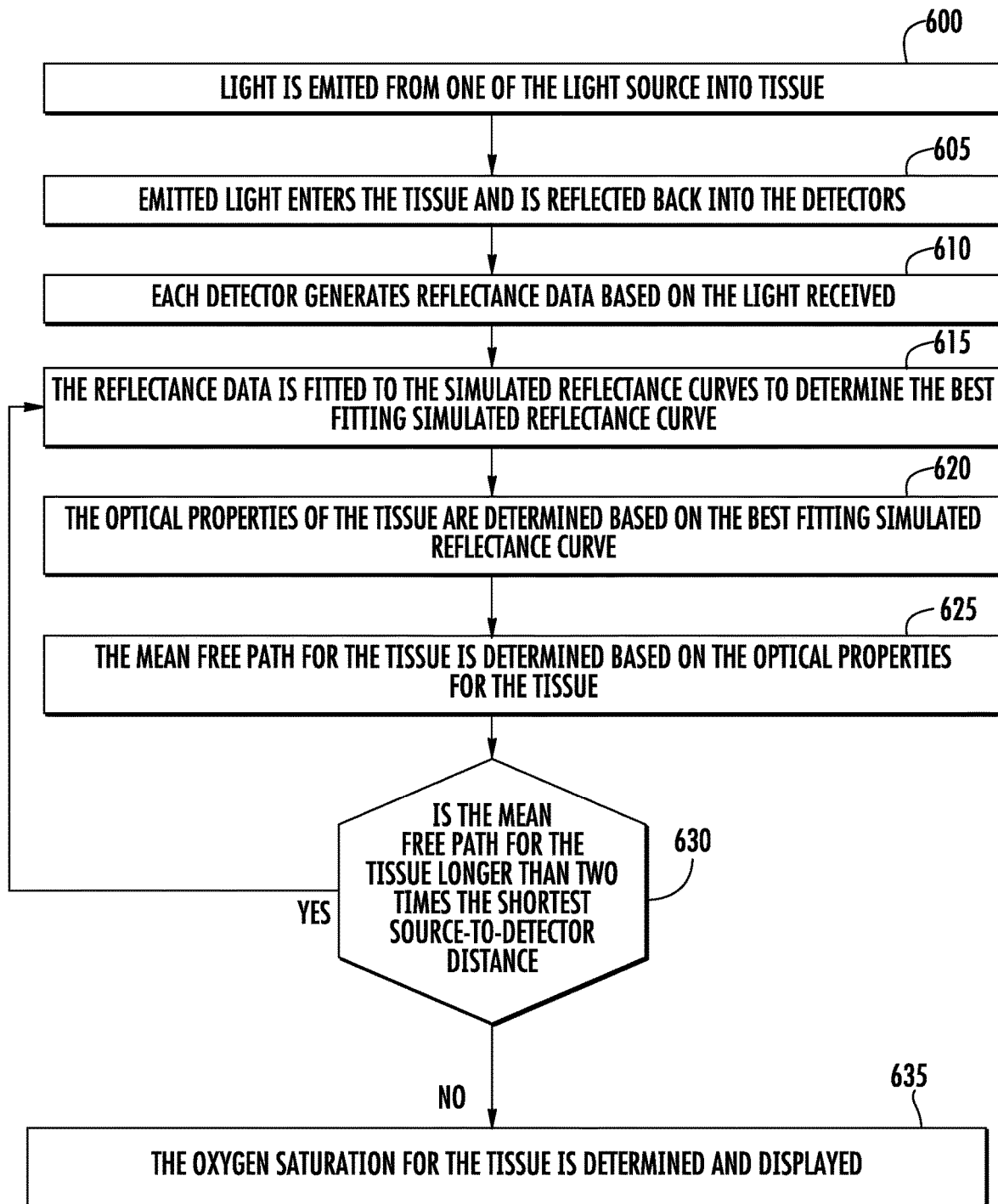
FIG. 6 is a high-level flow diagram of another method for determining the optical properties and tissue properties of real tissue by the tissue oximetry device.

FIG. 6 is a high-level flow diagram of another method for determining the optical properties of tissue by tissue oximetry device 100. The high-level flow diagram represents one example embodiment. Steps may be added to, removed from, or combined in the high-level flow diagram without deviating from the scope of the embodiment.

At 600, tissue oximetry device 100 emits light (e.g., near infrared light) from one of the light sources, such as light source 120a into tissue. After the emitted light reflects from the tissue, detectors 125 detect the light, step 605, and generate reflectance data for the tissue, step 610. Steps 600, 605, and 610 may be repeated for multiple wavelengths of light and for one or more other light sources, such as light source 120c. At 615, tissue oximetry device 100 fits the reflectance data to simulated reflectance curves 315 and determines the simulated reflectance curve to which the reflectance data has the best fit. Thereafter, tissue oximetry device 100 determines the optical properties (e.g., $\mu_a$, and $\mu_s'$) for the tissue based on the optical properties of the simulated reflectance curve that best fits the reflectance data, step 620.

At 625 tissue oximetry device 100 determines the mean free path of the light in the tissue from the optical properties (e.g., mfp=$1/(\mu_a+\mu_s')$) determined at step 620. Specifically, the mean free path can be determined from the optical properties obtained from a cumulative reflectance curve that includes the reflectance data for all of the source-detector pairs (e.g., pair 1: light source 120a-detector 125e; pair 2: light source 120a-detector 125f; pair 3: light source 120a-detector 125g; pair 4: light source 120a-detector 125h; pair 5: light source 120a-detector 125a; pair 6: light source 120a-detector 125b; pair 7: light source 120a-detector 125c; pair 8: light source 120a-detector 125d; . . . pair 9: light source 120c-detector 125e, pair 10: light source 120b-detector 125f . . . and others).

At 630, tissue oximetry device 100 determines whether the mean free path calculated for a given region of the tissue is longer than two times the shortest source-to-detector distance (e.g., D1 between light source 120a and detector 125e, and D9 between light source 120c and detector 125a). If the mean free path is longer than two times the shortest source-to-detector distance, then the collected reflectance data is re-fitted to the simulated reflectance curves (i.e., reanalyzed) without utilizing the reflectance data collected from the detectors for the source-to-detector pairs (e.g., pair 1: light source 120a-detector 125e and pair 9 light source 120c-detector 125a) having the shortest source-to-detector distance. For example, steps 615-630 are repeated without use of the reflectance data from detector 125e with light source 120a acting as the source for detector 125e, and without use of the reflectance data from detector 125a with light source 120c acting as the source for detector 125a. The process of calculating the mean free path and discarding the reflectance data for one or more source-detector pairs may be repeated until no source-detector pairs that contribute reflectance data to the fit have a source-to-detector distance shorter than one half of the calculated mean free path. Thereafter, oxygen saturation is determined from the best fitting simulated reflectance curve and reported by tissue oximetry device 110, such as on display 112, step 635.

Light that is emitted from one of the light sources 120 into tissue and that travels less than half of the mean free path is substantially non-diffusely reflected. The re-emission distance for this light is strongly dependent on the tissue phase function and the local tissue composition. Therefore, using the reflectance data for this light tends to result in a less accurate determination of the optical properties and tissue properties as compared with the reflectance data for light that has undergone multiple scattering events.

Data Weighting

Detectors 125 that are positioned at increasing distances from light sources 120 receive decreasing amounts of reflectance from tissue. Therefore, the reflectance data generated by detectors 125 having relatively short source-to-detector distances (e.g., D1) tends to exhibit intrinsically lower noise compared to reflectance data generated by detectors having relatively long source-to-detector distances (e.g., D5 and D10). Fit algorithms may therefore preferentially fit the simulated reflectance curves to the reflectance data that is generated by detectors 125 having relatively short source-to-detectors distances (e.g., source-to-detector distances less than or equal to the average distance between the light sources and the detectors) more tightly than reflectance data that is generated by detectors having relatively long source-to-detector distances (e.g., source-to-detector distances greater than the average distance). For relatively accurate determination of the optical properties from the reflectance data, this distance-proportional skew may be undesirable and may be corrected by weighting the reflectance data as described immediately below.

Figure 7:
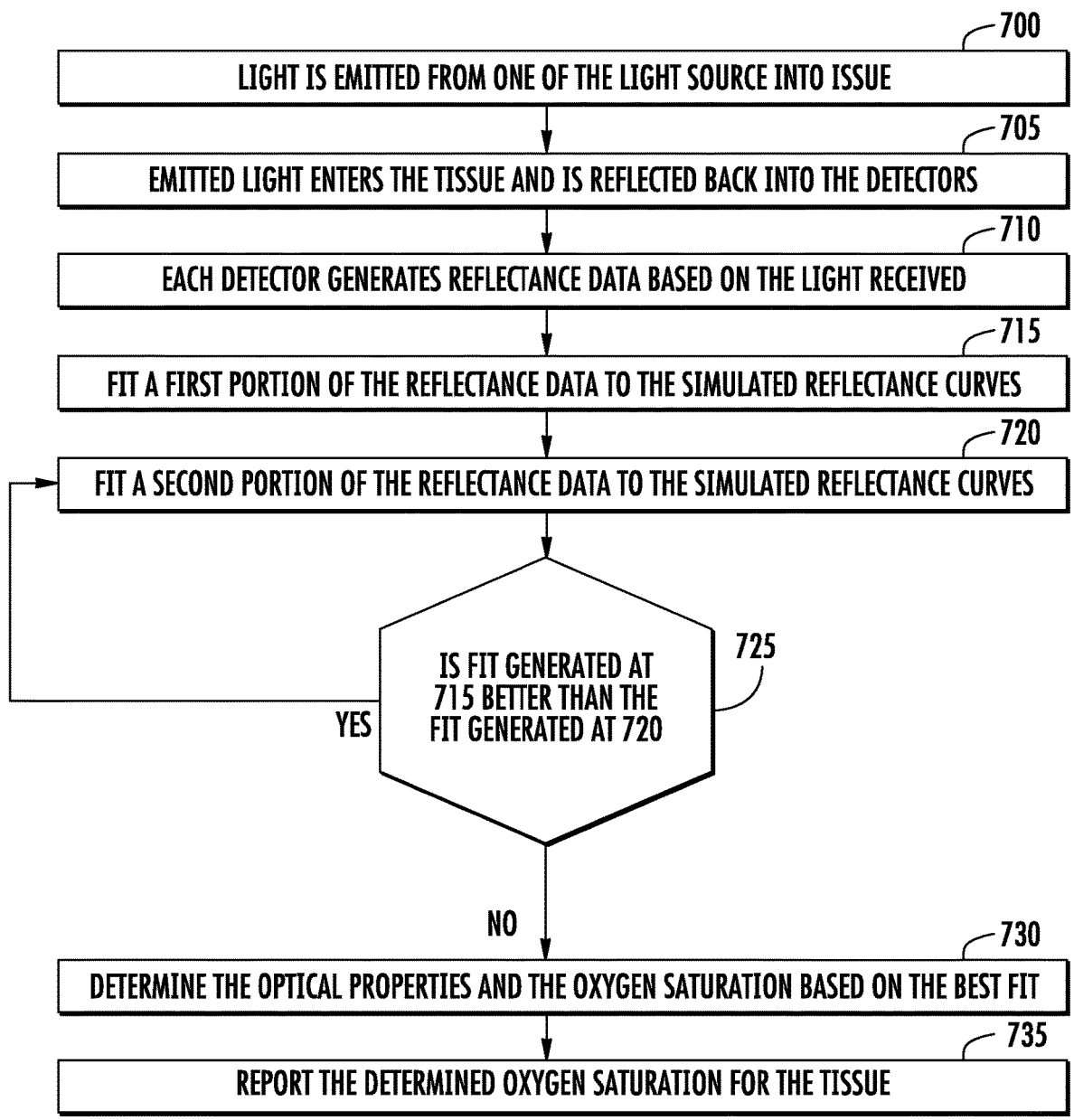
FIG. 7 is a high-level flow diagram of a method for weighting reflectance data generated by select detectors.

FIG. 7 is a high-level flow diagram of a method for weighting reflectance data generated by select detectors 125. The high-level flow diagram represents one example embodiment. Steps may be added to, removed from, or combined in the high-level flow diagram without deviating from the scope of the embodiment.

At 700, tissue oximetry device 100 emits light from one of the light sources, such as light source 120a into tissue. After the emitted light reflects from the tissue, detectors 125 detect the light, step 705, and generate reflectance data for the tissue, step 710. Steps 700, 705, and 710 may be repeated for multiple wavelengths of light and for one or more other light sources, such as light source 120c. At 715, tissue oximetry device 100 fits a first portion of the reflectance data to the simulated reflectance curves. The first portion of the reflectance data is generated by a first portion of detectors that are less than a threshold distance from the light source. The threshold distance may be the average distances (e.g., approximate mid-range distance) between the light sources and the detectors. At 720, reflectance data for a second portion of the reflectance data is fitted to the simulated reflectance curves. The second portion of reflectance data is generated by the first portion of the detectors and another detector that is at the next largest source-to-detector distance from the source compared to the threshold distance. For example, if the first portion of detectors includes detectors 125c, 125d, 125e, and 125f, then the detector that is at the next largest source-to-detector distance is detector 125g (e.g., closer to light source 120a than detector 125c, see FIGS. 2A and 2B).

At 725, the fit generated at step 715 is compared to the fit generated at step 720 to determine whether the fit generated at step 720 is better than the fit generated at 715. As will be understood by those of skill in the art, a "closeness" of a fit of data to a curve is quantifiable based on a variety of parameters, and the closeness of fits are directly comparable to determine the data having a closer fit (closer fit) to a curve. As will be further understood, a closer fit is sometimes also referred to as a better fit or a tighter fit. If the fit generated at step 720 is better than the fit generated at step 715, then steps 720 and 725 are repeated with reflectance data that is generated by detectors that include an additional detector (according to the example being considered, detector 125c) that is positioned at a next increased source-to-detector distance from the source. Alternatively, if the fit generated at step 720 is not better than the fit generated at step 715, then the reflectance data for detectors 125 that are positioned at source-to-detector distances that are greater than the threshold distance are not used in the fit. Thereafter, tissue oximetry device 100 uses the fit generated at 715 or step 720 (if better than the fit determined at step 715) to determine the optical properties and the oxygen saturation of the tissue, step 730. Thereafter, oxygen saturation is reported by tissue oximetry device 110, such as on display 112, step 735.

According to an alternative embodiment, if the fit generated at step 720 is not better than the fit generated at step 715, then the reflectance data are weighted by a weighting factor for detectors that have source-to-detector distances that are greater than the threshold distance so that this weighted reflectance data has a decreased influence on the fit. Reflectance data that is not used in a fit may be considered as having a zero weight and may be associated with reflectance from tissue below the tissue layer of interest. Reflectance from tissue below the tissue layer of interest is said to exhibit a characteristic kink in the reflectance curve that indicates this particular reflectance.

It is noted that curve-fitting algorithms that fit the reflectance data to the simulated reflectance curves may take into account the amount of uncertainty of the reflectance data as well as the absolute location of the reflectance data. Uncertainty in the reflectance data corresponds to the amount of noise from the generation of the reflectance data by one of the detectors, and the amount of noise can scale as the square root of the magnitude of the reflectance data.

According to a further embodiment, tissue oximetry device 100 iteratively weights the reflectance data based on the amount of noise associated with the measurements of the reflectance data. Specifically, the reflectance data generated by detectors having relatively large source-to-detector distances generally have greater a greater signal-to-noise ratio compared to the reflectance data generated by detector having relatively short source-to-detector distances. Weighting the reflectance data generated by detectors having relatively large source-to-detector distances allows for this data to contribute to the fit substantially equally to other reflectance data.

Calibration

According to one embodiment, tissue oximetry device 100 is calibrated utilizing a number (e.g., three to thirty) of tissue phantoms that have known optical properties. Tissue oximetry device 100 may be used to probe the tissue phantoms and collect reflectance data for the tissue phantoms. The reflectance data for each tissue phantom may be fitted to simulated reflectance curves 315. The reflectance data generated for each tissue phantom should fit a simulated reflectance curve, which has the same optical properties as the tissue phantom. If the optical properties of the simulated reflectance curve to which the reflectance data is fitted does not match the optical properties of the tissue phantom, then a calibration function may be generated by tissue oximetry device 100 to improve the fit. The calibration function for each of the tissue phantoms and matched simulated reflectance curves should substantially match. One or more of the calibration functions or an average of the calibration functions may be stored in memory 117. The one or more calibration functions may be applied to reflectance data generated for real tissue that is probed by tissue oximetry device 100 so that the reflectance data for the real tissue will fit to one of the simulated reflectance curves that has optical properties that are a substantially accurate match to the optical properties of the real tissue. Thereafter, the optical properties for the matched simulated reflectance curve may be used to calculate and report the oxygenation saturation of the real tissue.

Methods described herein for matching reflectance data to a number of Monte Carlo-simulated reflectance curves provides for relatively fast and accurate determination of the optical properties of real tissue probed by the tissue oximetry device. Speed in determining optical properties of tissue is an important consideration in the design of intraoperative probes compared to postoperative probes. Further, the Monte Carlo methods described herein allow for robust calibration methods that in-turn allow for the generation of absolute optical properties as compared with relative optical properties. Reporting absolute optical properties, as opposed to relative optical properties, is relatively important for intra-operative probes as compared with post-operative probes.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A device comprising:
a housing for a tissue oximeter device comprising a processor and nonvolatile memory contained within the housing, wherein the nonvolatile memory stores simulated reflectance curves, and the nonvolatile memory retains the simulated reflectance curves even when the device is powered off;
a display, coupled to the housing;
a battery source, contained by the housing;
a sensor head, coupled to and positioned at an end the housing, wherein the sensor head comprises a first source and a second source,
at least a first detector and a second detector, arranged on a first side of a first line passing through the first and second sources, wherein the first detector is a first distance from the first source, the second detector is a second distance from the first source, and the first distance is different from the second distance, and
at least a third detector and a fourth detector, arranged below a second side of the first line passing through the first and second sources, wherein the third detector is symmetric to the first detector about a first point on the first line, the fourth detector is symmetric to the second detector about the first point on the first line, and the processor is configured to cause:
emitting light from at least one of the first source and the second source of the sensor head into a tissue to be measured,
receiving by at least one of the first detector and the second detector of the tissue oximeter device light reflected from the tissue in response to the emitted light,
determine a plurality of digital reflectance data points for the reflected light,
retrieve the simulated reflectance curves from the nonvolatile memory, wherein the simulated reflectance curves were previously determined, before the processor determines the digital reflectance data points, based on the digital reflectance data points, determine a first subset of the simulated reflectance curves based on a coarse grid, wherein each curve in the first subset is separated by an interval from another curve of the first subset, calculate a closest fitting of the digital reflectance data points to a closest fit curve of the first subset of simulated reflectance curves, based on the digital reflectance data points, determine a second subset of the simulated reflectance curves based on a fine grid, and using the closest fit curve and second subset of simulated reflectance curves, calculate a set of absorption coefficients and a set of scattering coefficients for the reflectance data points, wherein the set of absorption coefficients and the set of scattering coefficients are used in the calculating an oxygen saturation value for the tissue; and based on the reflected light and the simulated reflectance curves stored in the nonvolatile memory, calculating an oxygen saturation value for the tissue and displaying this value at the display.

2. The device of claim 1 wherein a curve of the simulated reflectance curves comprises a first axis comprising a source-detector separation distance and a second axis comprising reflectance intensity.

3. The device of claim 2 wherein the curve comprises a first curve point having a first reflectance intensity at a first source-detector separation distance, and a second curve point having a second reflectance intensity at a second source-detector separation distance, for the first curve point, the first reflectance intensity is greater than the second reflectance intensity, and the first source-detector separation distance is less than the second source-detector separation distance, and for the second curve point, the second reflectance intensity is less than the first reflectance intensity, and the second source-detector separation distance greater then the first source-detector separation distance.

4. The device of claim 3 wherein the curve comprises a third curve point having a third reflectance intensity at a third source-detector separation distance, and a fourth curve point having a fourth reflectance intensity at a fourth source-detector separation distance, for the third curve point, the third reflectance intensity is greater than the fourth reflectance intensity, and the third source-detector separation distance is less than the fourth source-detector separation distance, and for the fourth curve point, the fourth reflectance intensity is less than the third reflectance intensity, and the fourth source-detector separation distance greater then the third source-detector separation distance, a first slope of a line through the first and second curve points is negative, and a second slope of a line through the third and fourth curve points is negative, and the second slope less negative than the first slope.

5. A device comprising:

a tissue oximetry device comprising a housing, wherein the tissue oximetry device is self-contained and comprises a sensor tip comprising a set of light sources, a plurality of detectors, memory, and a processor, the light sources and the detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the light sources and the detectors, and the processor causes:

transforming electrical signals generated by the processor into light using the light sources;

using the set of light sources of the tissue oximetry device, emitting the light having at least two wavelengths into tissue, and using the plurality of detectors of the tissue oximetry device, detecting light reflected in response to the light emitted into the tissue;

transforming the detected light into electrical signals using the detectors, wherein the electrical signals correspond to reflectance data points for the tissue;

generating digital reflectance data points for the tissue based on the electrical signals;

from the simulated data points, for the simulated reflectance intensities for the predetermined distances between the light sources and the detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves, and from the simulated data points, for the simulated reflectance intensities for the predetermined distances between the light sources and the detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;

from the simulated data points, for the simulated reflectance intensities for the predetermined distances between the light sources and the detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;

forming, by the processor housed in the housing, a first subset of simulated reflectance curves comprising the first, second, and third simulated reflectance curves, wherein the first subset is a subset on the coarse grid of the set of simulated reflectance curves stored in the memory and having the first and second interval values in the set of simulated reflectance curves stored in the memory;

using the processor of the tissue oximetry device, calculating a closest fitting of the digital reflectance data points to a closest fit curve of the first subset of simulated reflectance curves;

based on the closest fit curve, forming, by the processor housed in the housing, a second subset of simulated reflectance curves from the set of simulated reflectance curves, wherein the second subset is based on a fine grid;

using the closest fit curve and second subset of simulated reflectance curves, calculating a set of absorption coefficients and a set of scattering coefficients for the reflectance data points;

using the processor of the tissue oximetry device, calculating an oxygen saturation value for the tissue based on the set of absorption coefficients and disregarding the scattering coefficients when calculating the oxygen saturation value; and outputting an indication of the oxygen saturation value at an interface of the tissue oximetry device, wherein the interface of the tissue oximetry device comprises a liquid crystal display.

6. The device of claim 5 wherein the interface of the tissue oximetry device comprises light emitting diodes.

7. The device of claim 5 wherein the interface of the tissue oximetry device comprises a speaker.

8. The device of claim 5 wherein the using of the closest fit curve and second subset of simulated reflectance curves, calculating a set of absorption coefficients and a set of scattering coefficients for the reflectance data points comprises:

positioning the closest fit curve a center of the fine grid of the second subset of simulated reflectance curves;

using the fine grid with the closest fit curve at the center, determining a peak surface array of absorption coefficients and reflection scattering coefficients; and calculating a centroid calculation of the absorption coefficients and scattering coefficients from the peak surface array to determine the set of absorption coefficients and the set of scattering coefficients for the reflectance data points.

9. The device of claim 8 wherein the absorption coefficients and the scattering coefficients for the reflectance data points are independent from each other.

10. The device of claim 5 wherein the simulated reflectance curves were previously determined, before the digital reflectance data points are determined.

11. The device of claim 5 comprising disregarding the set of scattering coefficients when calculating the oxygen saturation value for the tissue.

12. The device of claim 5 wherein the absorption coefficients and the scattering coefficients for the reflectance data points are independent from each other when the scattering coefficients and the scattering coefficients for the reflectance data points are determined.

13. The device of claim 5 wherein at a first frequency repetitively performing transforming the detected light into electrical signals using the detectors, wherein at a second frequency repetitively performing:

from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;

forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating the closest fitting of the digital reflectance data points to the closest fit curve of the first subset of simulated reflectance curves;

based on the closest fit curve, forming, by the processor housed in the housing, the second subset of simulated reflectance curves from the set of simulated reflectance curves, wherein the second subset is based on the fine grid;

using the closest fit curve and second subset of simulated reflectance curves, calculating the set of absorption coefficients and the set of scattering coefficients for the reflectance data points; and using the processor of the tissue oximetry device, calculating the oxygen saturation value for the tissue based on the set of absorption coefficients and disregarding the scattering coefficients when calculating the oxygen saturation value, and wherein at a third frequency repetitively performing outputting the indication of the oxygen saturation value at the interface of the tissue oximetry device, and the first, second, and third frequencies are different frequencies.

14. The device of claim 13 wherein the first frequency is greater than the second and third frequencies and the second frequency is greater than the third frequency.

15. The device of claim 5 wherein the processor of the tissue oximeter device is not used to calculate the simulated reflectance curves.

16. A device comprising:

a tissue oximetry device comprising a housing, wherein the tissue oximetry device is self-contained and comprises a sensor tip comprising a set of light sources, a plurality of detectors, memory, and a processor, the light sources and the detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the light sources and the detectors, and the processor causes:

transforming electrical signals generated by the processor into light using the light sources;
using the set of light sources of the tissue oximetry device, emitting the light having at least a first wavelength and a second wavelength into the tissue;
using the plurality of detectors of the tissue oximetry device, detecting light reflected in response to the light emitted into the tissue;
at a first frequency repetitively performing transforming the detected light into electrical signals using the detectors, wherein the electrical signals correspond to digital reflectance data points for the tissue;
at a second frequency repetitively performing:
selecting, by the processor housed in the housing, a first selected simulated reflectance curve from the set of simulated reflectance curves stored in the memory to form a coarse grid of the set of simulated reflectance curves;
selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;
selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;
forming, by the processor housed in the housing, a first subset of simulated reflectance curves comprising the first, second, and third simulated reflectance curves, wherein the first subset is a subset of the coarse grid of the set of simulated reflectance curves stored in the memory and having the first and second interval values in the set of simulated reflectance curves stored in the memory;
using the processor of the tissue oximetry device, calculating a closest fitting of the digital reflectance data points to a closest fit curve of the first subset of simulated reflectance curves;
based on the closest fit curve, forming, by the processor housed in the housing, a second subset of simulated reflectance curves from the set of simulated reflectance curves, wherein the second subset is based on a fine grid;
using the closest fit curve and second subset of simulated reflectance curves, calculating a set of absorption coefficients for the reflectance data points; and
using the processor of the tissue oximetry device, calculating an oxygen saturation value for the tissue based on the set of absorption coefficients; and
outputting an indication of the oxygen saturation value at an interface of the tissue oximetry device, wherein the first and second frequencies are different frequencies; and
at the third frequency repetitively performing outputting the indication of the oxygen saturation value at the interface of the tissue oximetry device comprises updating the output on the display of the indication of the oxygen saturation value, wherein the first, second, and third frequencies are different frequencies.

17. The device of claim 16 wherein the first frequency is greater than the second and third frequencies.

18. A device comprising:
a tissue oximetry device comprising a housing, wherein the tissue oximetry device is self-contained and comprises a sensor tip comprising a set of light sources, a plurality of detectors, memory, and a processor, the light sources and the detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the light sources and the detectors, and the processor causes:
transforming electrical signals generated by the processor into light using the light sources;
using the set of light sources of the tissue oximetry device, emitting the light having at least two wavelengths into tissue;
using the plurality of detectors of the tissue oximetry device, detecting light reflected in response to the light emitted into the tissue;
transforming the detected light into electrical signals using the detectors, wherein the electrical signals correspond to reflectance data points for the tissue;
generating digital reflectance data points for the tissue based on the electrical signals;
from the simulated data points, for the simulated reflectance intensities for the predetermined distances between the light sources and the detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves;
from the simulated data points, for the simulated reflectance intensities for the predetermined distances between the light sources and the detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;
from the simulated data points, for the simulated reflectance intensities for the predetermined distances between the light sources and the detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;
forming, by the processor housed in the housing, a first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating a closest fitting of the digital reflectance data points to a closest fit curve of the first subset of simulated reflectance curves;

based on the closest fit curve, forming, by the processor housed in the housing, a second subset of simulated reflectance curves from the set of simulated reflectance curves, wherein the second subset is based on a fine grid;

using the closest fit curve and second subset of simulated reflectance curves, calculating a set of absorption coefficients and a set of scattering coefficients for the reflectance data points;

using the processor of the tissue oximetry device, calculating an oxygen saturation value for the tissue based on the set of absorption coefficients and disregarding the scattering coefficients when calculating the oxygen saturation value; and outputting an indication of the oxygen saturation value at an interface of the tissue oximetry device, wherein the interface of the tissue oximetry device comprises light emitting diodes.

19. The device of claim 18 wherein the interface of the tissue oximetry device comprises a speaker.

20. The device of claim 18 wherein the using of the closest fit curve and second subset of simulated reflectance curves, calculating a set of absorption coefficients and a set of scattering coefficients for the reflectance data points comprises:

positioning the closest fit curve a center of the fine grid of the second subset of simulated reflectance curves;

using the fine grid with the closest fit curve at the center, determining a peak surface array of absorption coefficients and reflection scattering coefficients; and calculating a centroid calculation of the absorption coefficients and scattering coefficients from the peak surface array to determine the set of absorption coefficients and the set of scattering coefficients for the reflectance data points.

21. The device of claim 20 wherein the absorption coefficients and the scattering coefficients for the reflectance data points are independent from each other.

22. The device of claim 18 wherein the simulated reflectance curves were previously determined, before the digital reflectance data points are determined.

23. The device of claim 18 comprising disregarding the set of scattering coefficients when calculating the oxygen saturation value for the tissue.

24. The device of claim 18 wherein the absorption coefficients and the scattering coefficients for the reflectance data points are independent from each other when the scattering coefficients and the scattering coefficients for the reflectance data points are determined.

25. The device of claim 18 wherein at a first frequency repetitively performing transforming the detected light into electrical signals using the detectors, wherein at a second frequency repetitively performing:

from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;

forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating the closest fitting of the digital reflectance data points to the closest fit curve of the first subset of simulated reflectance curves;

based on the closest fit curve, forming, by the processor housed in the housing, the second subset of simulated reflectance curves from the set of simulated reflectance curves, wherein the second subset is based on the fine grid;

using the closest fit curve and second subset of simulated reflectance curves, calculating the set of absorption coefficients and the set of scattering coefficients for the reflectance data points; and using the processor of the tissue oximetry device, calculating the oxygen saturation value for the tissue based on the set of absorption coefficients and disregarding the scattering coefficients when calculating the oxygen saturation value, and wherein at a third frequency repetitively performing outputting the indication of the oxygen saturation value at the interface of the tissue oximetry device, and the first, second, and third frequencies are different frequencies.

26. The device of claim 25 wherein the first frequency is greater than the second and third frequencies and the second frequency is greater than the third frequency.

27. The device of claim 18 wherein the processor of the tissue oximeter device is not used to calculate the simulated reflectance curves.

28. A device comprising:

a tissue oximetry device comprising a housing, wherein the tissue oximetry device is self-contained and comprises a sensor tip comprising a set of light sources, a plurality of detectors, memory, and a processor, the light sources and the detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the light sources and the detectors, and the processor causes:

transforming electrical signals generated by the processor into light using the light sources;

using the set of light sources of the tissue oximetry device, emitting the light having at least two wavelengths into tissue;

using the plurality of detectors of the tissue oximetry device, detecting light reflected in response to the light emitted into the tissue;

transforming the detected light into electrical signals using the detectors, wherein the electrical signals correspond to reflectance data points for the tissue;

generating digital reflectance data points for the tissue based on the electrical signals;

from the simulated data points, for the simulated reflectance intensities for the predetermined distances between the light sources and the detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves;

from the simulated data points, for the simulated reflectance intensities for the predetermined distances between the light sources and the detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;

from the simulated data points, for the simulated reflectance intensities for the predetermined distances between the light sources and the detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;

forming, by the processor housed in the housing, a first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating a closest fitting of the digital reflectance data points to a closest fit curve of the first subset of simulated reflectance curves;

based on the closest fit curve, forming, by the processor housed in the housing, a second subset of simulated reflectance curves from the set of simulated reflectance curves, wherein the second subset is based on a fine grid;

using the closest fit curve and second subset of simulated reflectance curves, calculating a set of absorption coefficients and a set of scattering coefficients for the reflectance data points;

using the processor of the tissue oximetry device, calculating an oxygen saturation value for the tissue based on the set of absorption coefficients and disregarding the scattering coefficients when calculating the oxygen saturation value; and outputting an indication of the oxygen saturation value at an interface of the tissue oximetry device, wherein the interface of the tissue oximetry device comprises a speaker.

29. The device of claim 28 wherein the using of the closest fit curve and second subset of simulated reflectance curves, calculating a set of absorption coefficients and a set of scattering coefficients for the reflectance data points comprises:

positioning the closest fit curve a center of the fine grid of the second subset of simulated reflectance curves;

using the fine grid with the closest fit curve at the center, determining a peak surface array of absorption coefficients and reflection scattering coefficients; and calculating a centroid calculation of the absorption coefficients and scattering coefficients from the peak surface array to determine the set of absorption coefficients and the set of scattering coefficients for the reflectance data points.

30. The device of claim 29 wherein the absorption coefficients and the scattering coefficients for the reflectance data points are independent from each other.

31. The device of claim 28 wherein the simulated reflectance curves were previously determined, before the digital reflectance data points are determined.

32. The device of claim 28 comprising disregarding the set of scattering coefficients when calculating the oxygen saturation value for the tissue.

33. The device of claim 28 wherein the absorption coefficients and the scattering coefficients for the reflectance data points are independent from each other when the scattering coefficients and the scattering coefficients for the reflectance data points are determined.

34. The device of claim 28 wherein at a first frequency repetitively performing transforming the detected light into electrical signals using the detectors, wherein at a second frequency repetitively performing:

from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;

forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating the closest fitting of the digital reflectance data points to the closest fit curve of the first subset of simulated reflectance curves;

based on the closest fit curve, forming, by the processor housed in the housing, the second subset of simulated reflectance curves from the set of simulated reflectance curves, wherein the second subset is based on the fine grid;

using the closest fit curve and second subset of simulated reflectance curves, calculating the set of absorption coefficients and the set of scattering coefficients for the reflectance data points; and using the processor of the tissue oximetry device, calculating the oxygen saturation value for the tissue based on the set of absorption coefficients and disregarding the scattering coefficients when calculating the oxygen saturation value, and wherein at a third frequency repetitively performing outputting the indication of the oxygen saturation value at the interface of the tissue oximetry device, and the first, second, and third frequencies are different frequencies.

35. The device of claim 34 wherein the first frequency is greater than the second and third frequencies and the second frequency is greater than the third frequency.

36. The device of claim 28 wherein the processor of the tissue oximeter device is not used to calculate the simulated reflectance curves.

37. A device comprising:

a tissue oximetry device comprising a housing, wherein the tissue oximetry device is self-contained and comprises a sensor tip comprising a set of light sources, a plurality of detectors, memory, and a processor, the light sources and the detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the light sources and the detectors, and the processor causes:

transforming electrical signals generated by the processor into light using the light sources;

using the set of light sources of the tissue oximetry device, emitting the light having at least two wavelengths into tissue;

using the plurality of detectors of the tissue oximetry device, detecting light reflected in response to the light emitted into the tissue;

transforming the detected light into electrical signals using the detectors, wherein the electrical signals correspond to reflectance data points for the tissue;

generating digital reflectance data points for the tissue based on the electrical signals;

from the simulated data points, for the simulated reflectance intensities for the predetermined distances between the light sources and the detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves;

from the simulated data points, for the simulated reflectance intensities for the predetermined distances between the light sources and the detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;

from the simulated data points, for the simulated reflectance intensities for the predetermined distances between the light sources and the detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;

forming, by the processor housed in the housing, a first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating a closest fitting of the digital reflectance data points to a closest fit curve of the first subset of simulated reflectance curves;

based on the closest fit curve, forming, by the processor housed in the housing, a second subset of simulated reflectance curves from the set of simulated reflectance curves, wherein the second subset is based on a fine grid;

using the closest fit curve and second subset of simulated reflectance curves, calculating a set of absorption coefficients and a set of scattering coefficients for the reflectance data points;

using the processor of the tissue oximetry device, calculating an oxygen saturation value for the tissue based on the set of absorption coefficients and disregarding the scattering coefficients when calculating the oxygen saturation value; and outputting an indication of the oxygen saturation value at an interface of the tissue oximetry device, wherein the using of the closest fit curve and second subset of simulated reflectance curves, calculating a set of absorption coefficients and a set of scattering coefficients for the reflectance data points comprises:

positioning the closest fit curve a center of the fine grid of the second subset of simulated reflectance curves;

using the fine grid with the closest fit curve at the center, determining a peak surface array of absorption coefficients and reflection scattering coefficients; and calculating a centroid calculation of the absorption coefficients and scattering coefficients from the peak surface array to determine the set of absorption coefficients and the set of scattering coefficients for the reflectance data points.

38. The device of claim 37 wherein the absorption coefficients and the scattering coefficients for the reflectance data points are independent from each other.

39. The device of claim 37 wherein the simulated reflectance curves were previously determined, before the digital reflectance data points are determined.

40. The device of claim 37 comprising disregarding the set of scattering coefficients when calculating the oxygen saturation value for the tissue.

41. The device of claim 37 wherein the absorption coefficients and the scattering coefficients for the reflectance data points are independent from each other when the scattering coefficients and the scattering coefficients for the reflectance data points are determined.

42. The device of claim 37 wherein at a first frequency repetitively performing transforming the detected light into electrical signals using the detectors, wherein at a second frequency repetitively performing:
from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;

forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating the closest fitting of the digital reflectance data points to the closest fit curve of the first subset of simulated reflectance curves;

based on the closest fit curve, forming, by the processor housed in the housing, the second subset of simulated reflectance curves from the set of simulated reflectance curves, wherein the second subset is based on the fine grid;

using the closest fit curve and second subset of simulated reflectance curves, calculating the set of absorption coefficients and the set of scattering coefficients for the reflectance data points; and using the processor of the tissue oximetry device, calculating the oxygen saturation value for the tissue based on the set of absorption coefficients and disregarding the scattering coefficients when calculating the oxygen saturation value, and wherein at a third frequency repetitively performing outputting the indication of the oxygen saturation value at the interface of the tissue oximetry device, and the first, second, and third frequencies are different frequencies.

43. The device of claim 42 wherein the first frequency is greater than the second and third frequencies and the second frequency is greater than the third frequency.

44. The device of claim 37 wherein the processor of the tissue oximeter device is not used to calculate the simulated reflectance curves.

45. A device comprising:
a tissue oximetry device comprising a housing, wherein the tissue oximetry device is self-contained and comprises a sensor tip comprising a set of light sources, a plurality of detectors, memory, and a processor, the source and detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the source and detectors, and the processor causes:

transforming electrical signals generated by the processor into light using the light sources;

using the set of light sources of the tissue oximetry device, emitting the light having at least two wavelengths into tissue;

using the plurality of detectors of the tissue oximetry device, detecting light reflected in response to the light emitted into the tissue;

transforming the detected light into electrical signals using the detectors, wherein the electrical signals correspond to reflectance data points for the tissue;

generating digital reflectance data points for the tissue based on the electrical signals;

from the simulated data points, for the simulated reflectance intensities for the predetermined distances between the source and detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;

forming, by the processor housed in the housing, a first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating a closest fitting of the digital reflectance data points to a closest fit curve of the first subset of simulated reflectance curves;

based on the closest fit curve, forming, by the processor housed in the housing, a second subset of simulated reflectance curves from the set of simulated reflectance curves, wherein the second subset is based on a fine grid;

using the closest fit curve and second subset of simulated reflectance curves, calculating a set of absorption coefficients and a set of scattering coefficients for the reflectance data points;

using the processor of the tissue oximetry device, calculating an oxygen saturation value for the tissue based on the set of absorption coefficients and disregarding the scattering coefficients when calculating the oxygen saturation value; and outputting an indication of the oxygen saturation value at an interface of the tissue oximetry device, wherein the using of the closest fit curve and second subset of simulated reflectance curves, calculating a set of absorption coefficients and a set of scattering coefficients for the reflectance data points comprises:

positioning the closest fit curve a center of the fine grid of the second subset of simulated reflectance curves;

using the fine grid with the closest fit curve at the center, determining a peak surface array of absorption coefficients and reflection scattering coefficients; and calculating a centroid calculation of the absorption coefficients and scattering coefficients from the peak surface array to determine the set of absorption coefficients and the set of scattering coefficients for the reflectance data points, and wherein the absorption coefficients and the scattering coefficients for the reflectance data points are independent from each other.

46. The device of claim 45 wherein the interface of the tissue oximetry device comprises light emitting diodes.

47. The device of claim 45 wherein the interface of the tissue oximetry device comprises a speaker.

48. The device of claim 45 wherein the simulated reflectance curves were previously determined, before the digital reflectance data points are determined.

49. The device of claim 45 comprising disregarding the set of scattering coefficients when calculating the oxygen saturation value for the tissue.

50. The device of claim 45 wherein the absorption coefficients and the scattering coefficients for the reflectance data points are independent from each other when the scattering coefficients and the scattering coefficients for the reflectance data points are determined.

51. The device of claim 45 wherein at a first frequency repetitively performing transforming the detected light into electrical signals using the detectors, wherein at a second frequency repetitively performing:

from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;

forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating the closest fitting of the digital reflectance data points to the closest fit curve of the first subset of simulated reflectance curves;

based on the closest fit curve, forming, by the processor housed in the housing, the second subset of simulated reflectance curves from the set of simulated reflectance curves, wherein the second subset is based on the fine grid;

using the closest fit curve and second subset of simulated reflectance curves, calculating the set of absorption coefficients and the set of scattering coefficients for the reflectance data points; and using the processor of the tissue oximetry device, calculating the oxygen saturation value for the tissue based on the set of absorption coefficients and disregarding the scattering coefficients when calculating the oxygen saturation value, and wherein at a third frequency repetitively performing outputting the indication of the oxygen saturation value at the interface of the tissue oximetry device, and the first, second, and third frequencies are different frequencies.

52. The device of claim 51 wherein the first frequency is greater than the second and third frequencies and the second frequency is greater than the third frequency.

53. The device of claim 45 wherein the processor of the tissue oximeter device is not used to calculate the simulated reflectance curves.

54. A device comprising:

a tissue oximetry device comprising a housing, wherein the tissue oximetry device is self-contained and comprises a sensor tip comprising a set of light sources, a plurality of detectors, memory, and a processor, the light sources and the detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the light sources and the detectors, and the processor causes:

transforming electrical signals generated by the processor into light using the light sources;

using the set of light sources of the tissue oximetry device, emitting the light having at least two wavelengths into tissue;

using the plurality of detectors of the tissue oximetry device, detecting light reflected in response to the light emitted into the tissue;

transforming the detected light into electrical signals using the detectors, wherein the electrical signals correspond to reflectance data points for the tissue;

generating digital reflectance data points for the tissue based on the electrical signals;

from the simulated data points, for the simulated reflectance intensities for the predetermined distances between the light sources and the detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves;

from the simulated data points, for the simulated reflectance intensities for the predetermined distances between the light sources and the detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;

from the simulated data points, for the simulated reflectance intensities for the predetermined distances between the light sources and the detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;

forming, by the processor housed in the housing, a first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating a closest fitting of the digital reflectance data points to a closest fit curve of the first subset of simulated reflectance curves;

based on the closest fit curve, forming, by the processor housed in the housing, a second subset of simulated reflectance curves from the set of simulated reflectance curves, wherein the second subset is based on a fine grid;

using the closest fit curve and second subset of simulated reflectance curves, calculating a set of absorption coefficients and a set of scattering coefficients for the reflectance data points;

using the processor of the tissue oximetry device, calculating an oxygen saturation value for the tissue based on the set of absorption coefficients and disregarding the scattering coefficients when calculating the oxygen saturation value; and outputting an indication of the oxygen saturation value at an interface of the tissue oximetry device, wherein the simulated reflectance curves were previously determined, before the digital reflectance data points are determined.

55. The device of claim 54 comprising disregarding the set of scattering coefficients when calculating the oxygen saturation value for the tissue.

56. The device of claim 54 wherein the absorption coefficients and the scattering coefficients for the reflectance data points are independent from each other when the scattering coefficients and the scattering coefficients for the reflectance data points are determined.

57. The device of claim 54 wherein at a first frequency repetitively performing transforming the detected light into electrical signals using the detectors,
  wherein at a second frequency repetitively performing:
    from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;
    from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;
    from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;
    forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;
    using the processor of the tissue oximetry device, calculating the closest fitting of the digital reflectance data points to the closest fit curve of the first subset of simulated reflectance curves;
    based on the closest fit curve, forming, by the processor housed in the housing, the second subset of simulated reflectance curves from the set of simulated reflectance curves, wherein the second subset is based on the fine grid;
    using the closest fit curve and second subset of simulated reflectance curves, calculating the set of absorption coefficients and the set of scattering coefficients for the reflectance data points; and
    using the processor of the tissue oximetry device, calculating the oxygen saturation value for the tissue based on the set of absorption coefficients and disregarding the scattering coefficients when calculating the oxygen saturation value, and
  wherein at a third frequency repetitively performing outputting the indication of the oxygen saturation value at the interface of the tissue oximetry device, and the first, second, and third frequencies are different frequencies.

58. The device of claim 57 wherein the first frequency is greater than the second and third frequencies and the second frequency is greater than the third frequency.

59. The device of claim 54 wherein the processor of the tissue oximeter device is not used to calculate the simulated reflectance curves.

60. A device comprising:
  a tissue oximetry device comprising a housing, wherein the tissue oximetry device is self-contained and comprises a sensor tip comprising a set of light sources, a plurality of detectors, memory, and a processor, the light sources and the detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the light sources and the detectors, and the processor causes:
  transforming electrical signals generated by the processor into light using the light sources;
  using the set of light sources of the tissue oximetry device, emitting the light having at least two wavelengths into tissue;
  using the plurality of detectors of the tissue oximetry device, detecting light reflected in response to the light emitted into the tissue;
  transforming the detected light into electrical signals using the detectors, wherein the electrical signals correspond to reflectance data points for the tissue;
  generating digital reflectance data points for the tissue based on the electrical signals;
  from the simulated data points, for the simulated reflectance intensities for the predetermined distances between the light sources and the detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves;
  from the simulated data points, for the simulated reflectance intensities for the predetermined distances between the light sources and the detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;
  from the simulated data points, for the simulated reflectance intensities for the predetermined distances between the light sources and the detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;

forming, by the processor housed in the housing, a first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating a closest fitting of the digital reflectance data points to a closest fit curve of the first subset of simulated reflectance curves;

based on the closest fit curve, forming, by the processor housed in the housing, a second subset of simulated reflectance curves from the set of simulated reflectance curves, wherein the second subset is based on a fine grid;

using the closest fit curve and second subset of simulated reflectance curves, calculating a set of absorption coefficients and a set of scattering coefficients for the reflectance data points;

using the processor of the tissue oximetry device, calculating an oxygen saturation value for the tissue based on the set of absorption coefficients and disregarding the scattering coefficients when calculating the oxygen saturation value when calculating the oxygen saturation value for the tissue; and outputting an indication of the oxygen saturation value at an interface of the tissue oximetry device.

61. The device of claim 60 wherein the absorption coefficients and the scattering coefficients for the reflectance data points are independent from each other when the scattering coefficients and the scattering coefficients for the reflectance data points are determined.

62. The device of claim 60 wherein at a first frequency repetitively performing transforming the detected light into electrical signals using the detectors, wherein at a second frequency repetitively performing:

from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;

forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating the closest fitting of the digital reflectance data points to the closest fit curve of the first subset of simulated reflectance curves;

based on the closest fit curve, forming, by the processor housed in the housing, the second subset of simulated reflectance curves from the set of simulated reflectance curves, wherein the second subset is based on the fine grid;

using the closest fit curve and second subset of simulated reflectance curves, calculating the set of absorption coefficients and the set of scattering coefficients for the reflectance data points; and using the processor of the tissue oximetry device, calculating the oxygen saturation value for the tissue based on the set of absorption coefficients and disregarding the scattering coefficients when calculating the oxygen saturation value, and wherein at a third frequency repetitively performing outputting the indication of the oxygen saturation value at the interface of the tissue oximetry device, and the first, second, and third frequencies are different frequencies.

63. The device of claim 62 wherein the first frequency is greater than the second and third frequencies and the second frequency is greater than the third frequency.

64. The device of claim 60 wherein the processor of the tissue oximeter device is not used to calculate the simulated reflectance curves.

65. A device comprising:

a tissue oximetry device comprising a housing, wherein the tissue oximetry device is self-contained and comprises a sensor tip comprising a set of light sources, a plurality of detectors, memory, and a processor, the light sources and the detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the light sources and the detectors, and the processor causes:

transforming electrical signals generated by the processor into light using the light sources;

using the set of light sources of the tissue oximetry device, emitting the light having at least two wavelengths into tissue;

using the plurality of detectors of the tissue oximetry device, detecting light reflected in response to the light emitted into the tissue;

transforming the detected light into electrical signals using the detectors, wherein the electrical signals correspond to reflectance data points for the tissue;

generating digital reflectance data points for the tissue based on the electrical signals;

from the simulated data points, for the simulated reflectance intensities for the predetermined distances between the light sources and the detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves;

from the simulated data points, for the simulated reflectance intensities for the predetermined distances between the light sources and the detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;

from the simulated data points, for the simulated reflectance intensities for the predetermined distances between the light sources and the detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;

forming, by the processor housed in the housing, a first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating a closest fitting of the digital reflectance data points to a closest fit curve of the first subset of simulated reflectance curves;

based on the closest fit curve, forming, by the processor housed in the housing, a second subset of simulated reflectance curves from the set of simulated reflectance curves, wherein the second subset is based on a fine grid;

using the closest fit curve and second subset of simulated reflectance curves, calculating a set of absorption coefficients and a set of scattering coefficients for the reflectance data points;

using the processor of the tissue oximetry device, calculating an oxygen saturation value for the tissue based on the set of absorption coefficients and disregarding the scattering coefficients when calculating the oxygen saturation value; and outputting an indication of the oxygen saturation value at an interface of the tissue oximetry device, wherein the absorption coefficients and the scattering coefficients for the reflectance data points are independent from each other when the scattering coefficients and the scattering coefficients for the reflectance data points are determined.

66. The device of claim 65 wherein at a first frequency repetitively performing transforming the detected light into electrical signals using the detectors, wherein at a second frequency repetitively performing:

from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;

forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating the closest fitting of the digital reflectance data points to the closest fit curve of the first subset of simulated reflectance curves;

based on the closest fit curve, forming, by the processor housed in the housing, the second subset of simulated reflectance curves from the set of simulated reflectance curves, wherein the second subset is based on the fine grid;

using the closest fit curve and second subset of simulated reflectance curves, calculating the set of absorption coefficients and the set of scattering coefficients for the reflectance data points; and using the processor of the tissue oximetry device, calculating the oxygen saturation value for the tissue based on the set of absorption coefficients and disregarding the scattering coefficients when calculating the oxygen saturation value, and wherein at a third frequency repetitively performing outputting the indication of the oxygen saturation value at the interface of the tissue oximetry device, and the first, second, and third frequencies are different frequencies.

67. The device of claim 66 wherein the first frequency is greater than the second and third frequencies and the second frequency is greater than the third frequency.

68. The device of claim 65 wherein the processor of the tissue oximeter device is not used to calculate the simulated reflectance curves.

69. A device comprising:
a tissue oximetry device comprising a housing, wherein the tissue oximetry device is self-contained and comprises a sensor tip comprising a set of light sources, a plurality of detectors, memory, and a processor, the light sources and the detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the light sources and the detectors, and the processor causes:
transforming electrical signals generated by the processor into light using the light sources;
using the set of light sources of the tissue oximetry device, emitting the light having at least two wavelengths into tissue;
using the plurality of detectors of the tissue oximetry device, detecting light reflected in response to the light emitted into the tissue;
transforming the detected light into electrical signals using the detectors, wherein the electrical signals correspond to reflectance data points for the tissue;
generating digital reflectance data points for the tissue based on the electrical signals;
from the simulated data points, for the simulated reflectance intensities for the predetermined distances between the light sources and the detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves;
from the simulated data points, for the simulated reflectance intensities for the predetermined distances between the light sources and the detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;
from the simulated data points, for the simulated reflectance intensities for the predetermined distances between the light sources and the detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;
forming, by the processor housed in the housing, a first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;
using the processor of the tissue oximetry device, calculating a closest fitting of the digital reflectance data points to a closest fit curve of the first subset of simulated reflectance curves;
based on the closest fit curve, forming, by the processor housed in the housing, a second subset of simulated reflectance curves from the set of simulated reflectance curves, wherein the second subset is based on a fine grid;
using the closest fit curve and second subset of simulated reflectance curves, calculating a set of absorption coefficients and a set of scattering coefficients for the reflectance data points;
using the processor of the tissue oximetry device, calculating an oxygen saturation value for the tissue based on the set of absorption coefficients and disregarding the scattering coefficients when calculating the oxygen saturation value; and
outputting an indication of the oxygen saturation value at an interface of the tissue oximetry device, wherein at a first frequency repetitively performing transforming the detected light into electrical signals using the detectors, wherein at a second frequency repetitively performing:
from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;
from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;
from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;
forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating the closest fitting of the digital reflectance data points to the closest fit curve of the first subset of simulated reflectance curves;

based on the closest fit curve, forming, by the processor housed in the housing, the second subset of simulated reflectance curves from the set of simulated reflectance curves, wherein the second subset is based on the fine grid;

using the closest fit curve and second subset of simulated reflectance curves, calculating the set of absorption coefficients and the set of scattering coefficients for the reflectance data points; and using the processor of the tissue oximetry device, calculating the oxygen saturation value for the tissue based on the set of absorption coefficients and disregarding the scattering coefficients when calculating the oxygen saturation value, and wherein at a third frequency repetitively performing outputting the indication of the oxygen saturation value at the interface of the tissue oximetry device, and the first, second, and third frequencies are different frequencies.

70. The device of claim 69 wherein the first frequency is greater than the second and third frequencies and the second frequency is greater than the third frequency.

71. The device of claim 69 wherein the processor of the tissue oximeter device is not used to calculate the simulated reflectance curves.

72. A device comprising:
a tissue oximetry device comprising a housing, wherein the tissue oximetry device is self-contained and comprises a sensor tip comprising a set of light sources, a plurality of detectors, memory, and a processor, the source and detectors are separated by predetermined distances, and the memory stores a set of simulated reflectance curves, each simulated reflectance curve of the set of simulated reflectance curves is based on a simulation of light reflected from simulated tissue, simulated data points of simulated reflectance intensities of the simulated reflectance curves are for the predetermined distances between the source and detectors, and the processor causes:

transforming electrical signals generated by the processor into light using the light sources;

using the set of light sources of the tissue oximetry device, emitting the light having at least two wavelengths into tissue;

using the plurality of detectors of the tissue oximetry device, detecting light reflected in response to the light emitted into the tissue;

transforming the detected light into electrical signals using the detectors, wherein the electrical signals correspond to reflectance data points for the tissue;

generating digital reflectance data points for the tissue based on the electrical signals;

from the simulated data points, for the simulated reflectance intensities for the predetermined distances between the source and detectors, for the set of simulated reflectance curves stored in the memory of the tissue oximetry device, selecting, by the processor housed in the housing, a first selected simulated reflectance curve from the set of simulated reflectance curves stored in the memory to form a coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, a second selected simulated reflectance curve from the set of simulated reflectance curves stored in the memory to form the coarse grid of the set of simulated reflectance curves, wherein the second selected simulated reflectance curve is a first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, a third selected simulated reflectance curve from the set of simulated reflectance curves stored in the memory to form the coarse grid of the set of simulated reflectance curves, wherein the third selected simulated reflectance curve is a second interval value away from the second simulated reflectance curve;

forming, by the processor housed in the housing, a first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating a closest fitting of the digital reflectance data points to a closest fit curve of the first subset of simulated reflectance curves;

based on the closest fit curve, forming, by the processor housed in the housing, a second subset of simulated reflectance curves from the set of simulated reflectance curves, wherein the second subset is based on a fine grid;

using the closest fit curve and second subset of simulated reflectance curves, calculating a set of absorption coefficients and a set of scattering coefficients for the reflectance data points;

using the processor of the tissue oximetry device, calculating an oxygen saturation value for the tissue based on the set of absorption coefficients and disregarding the scattering coefficients when calculating the oxygen saturation value; and outputting an indication of the oxygen saturation value at an interface of the tissue oximetry device, wherein at a first frequency repetitively performing transforming the detected light into electrical signals using the detectors, wherein at a second frequency repetitively performing:

from the simulated data points, for the simulated reflectance intensities for the predetermined distances between the source and detectors, for the set of simulated reflectance curves stored in the memory of the tissue oximetry device, selecting, by the processor housed in the housing, the first selected simulated reflectance curve from the set of simulated reflectance curves stored in the memory to form the coarse grid of the set of simulated reflectance curves;

from the simulated data points, for the simulated reflectance intensities for the predetermined distances between the source and detectors, for the set of simulated reflectance curves stored in the memory of the tissue oximetry device, selecting, by the processor housed in the housing, the second selected simulated reflectance curve from the set of simulated reflectance curves stored in the memory to form the coarse grid of the set of simulated reflectance curves, wherein the second selected simulated reflectance curve is the first interval value away from the first simulated reflectance curve;

from the simulated data points, for the simulated reflectance intensities for the predetermined distances between the source and detectors, for the set of simulated reflectance curves stored in the memory of the tissue oximetry device, selecting, by the processor housed in the housing, the third selected simulated reflectance curve from the set of simulated reflectance curves stored in the memory to form the coarse grid of the set of simulated reflectance curves, wherein the third selected simulated reflectance curve is the second interval value away from the second simulated reflectance curve;

forming, by the processor housed in the housing, the first subset of simulated reflectance curves comprising the first, second, and third simulated reflectance curves, wherein the first subset is based on the coarse grid of the set of simulated reflectance curves stored in the memory and having the first and second interval values in the set of simulated reflectance curves stored in the memory;

using the processor of the tissue oximetry device, calculating the closest fitting of the digital reflectance data points to the closest fit curve of the first subset of simulated reflectance curves;

based on the closest fit curve, forming, by the processor housed in the housing, the second subset of simulated reflectance curves from the set of simulated reflectance curves, wherein the second subset is based on the fine grid;

using the closest fit curve and second subset of simulated reflectance curves, calculating the set of absorption coefficients and the set of scattering coefficients for the reflectance data points; and using the processor of the tissue oximetry device, calculating the oxygen saturation value for the tissue based on the set of absorption coefficients and disregarding the scattering coefficients when calculating the oxygen saturation value, and wherein at a third frequency repetitively performing outputting the indication of the oxygen saturation value at the interface of the tissue oximetry device, and the first, second, and third frequencies are different frequencies, and wherein the first frequency is greater than the second and third frequencies and the second frequency is greater than the third frequency.

73. The device of claim 72 wherein the interface of the tissue oximetry device comprises a liquid crystal display.

74. The device of claim 72 wherein the interface of the tissue oximetry device comprises light emitting diodes.

75. The device of claim 72 wherein the interface of the tissue oximetry device comprises a speaker.

76. The device of claim 72 wherein the using of the closest fit curve and second subset of simulated reflectance curves, calculating a set of absorption coefficients and a set of scattering coefficients for the reflectance data points comprises:

positioning the closest fit curve a center of the fine grid of the second subset of simulated reflectance curves;

using the fine grid with the closest fit curve at the center, determining a peak surface array of absorption coefficients and reflection scattering coefficients; and calculating a centroid calculation of the absorption coefficients and scattering coefficients from the peak surface array to determine the set of absorption coefficients and the set of scattering coefficients for the reflectance data points.

77. The device of claim 76 wherein the absorption coefficients and the scattering coefficients for the reflectance data points are independent from each other.

78. The device of claim 72 wherein the simulated reflectance curves were previously determined, before the digital reflectance data points are determined.

79. The device of claim 72 comprising disregarding the set of scattering coefficients when calculating the oxygen saturation value for the tissue.

80. The device of claim 72 wherein the absorption coefficients and the scattering coefficients for the reflectance data points are independent from each other when the scattering coefficients and the scattering coefficients for the reflectance data points are determined.

81. The device of claim 72 wherein the processor of the tissue oximeter device is not used to calculate the simulated reflectance curves.

* * * * *